United States Patent
Gerstenberger et al.

(10) Patent No.: US 11,655,252 B2
(45) Date of Patent: May 23, 2023

(54) AMINOPYRIMIDINYL DERIVATIVES

(71) Applicant: Pfizer Inc., New York, NY (US)

(72) Inventors: Brian Stephen Gerstenberger, Cambridge, MA (US); Wenhua Jiao, Salem, CT (US); Manjinder Singh Lall, East Lyme, CT (US); Ricardo Lira, East Lyme, CT (US); Mark Edward Schnute, Acton, MA (US)

(73) Assignee: Pfizer Inc., New York, NY (US)

( * ) Notice: Subject to any disclaimer, the term of this patent is extended or adjusted under 35 U.S.C. 154(b) by 80 days.

(21) Appl. No.: 17/363,494

(22) Filed: Jun. 30, 2021

(65) Prior Publication Data

US 2022/0002301 A1 Jan. 6, 2022

Related U.S. Application Data

(60) Provisional application No. 63/047,606, filed on Jul. 2, 2020.

(51) Int. Cl.
*C07D 471/18* (2006.01)
*A61K 45/06* (2006.01)

(52) U.S. Cl.
CPC ............ *C07D 471/18* (2013.01); *A61K 45/06* (2013.01); *C07B 2200/13* (2013.01)

(58) Field of Classification Search
CPC .............................. C07D 471/18; A61K 45/06
See application file for complete search history.

(56) References Cited

U.S. PATENT DOCUMENTS

| | | | | |
|---|---|---|---|---|
| 9,187,453 B2 * | 11/2015 | Tsukamoto | ............ | A61P 19/02 |
| 9,663,526 B2 * | 5/2017 | Fensome | .................. | A61P 19/10 |
| 10,463,675 B2 * | 11/2019 | Fensome | .................. | A61P 31/04 |
| 10,980,815 B2 * | 4/2021 | Fensome | .................. | A61P 35/02 |
| 11,197,867 B2 * | 12/2021 | Fensome | ............. | C07D 403/14 |
| 2016/0000784 A1 * | 1/2016 | Newton | .................. | A61P 31/04 544/70 |
| 2020/0330477 A1 * | 10/2020 | Fensome | .................. | A61P 1/16 |
| 2021/0377495 A1 * | 12/2021 | Fensome | .................. | A61P 19/06 |

FOREIGN PATENT DOCUMENTS

| | | | | |
|---|---|---|---|---|
| WO | WO-2012062704 A1 * | 5/2012 | ........... | C07D 239/42 |
| WO | 2016/027195 A1 | 2/2016 | | |
| WO | WO-2020259584 A1 * | 12/2020 | ................ | A61P 1/00 |

OTHER PUBLICATIONS

Fensome; J. Med. Chem. 2018, 61, 8597-8612. http://dx.doi.org/10.1021/acs.jmedchem.8b00917 (Year: 2018).*
Kisseleva et al., "Signaling through the JAK/STAT pathway, recent advances and future challenges", Gene, 2002, 285, 1-24.
Murray, "The JAK-STAT Signaling Pathway: Input and Output Integration", Journal of Immunology, 2007, 178, 2623-2629.
O'SHEA et al., "JAK and STAT Signaling Molecules in Immunoregulation and Immune-Mediated Disease", Immunity, 2012, 36, 542-550.
Yamaoka et al., "Protein family review, The Janus kinases (Jaks)", Genome Biology, 2004, 5, 253.
Fensome et al., "Design and Optimization of a series of 4-(3-azabicyclo[3.1.0]hexan-3-yl)pyrimidin-2-amines: Dual inhibitors of TYK2 and JAK1", Bioorganic & Medicinal Chemistry, 2020, 28(10), 1-11.
International Search Report & Written Opinion dated Sep. 3, 2021, for International application No. PCT/IB2021/055851, filed Jun. 30, 2021.

* cited by examiner

*Primary Examiner* — Daniel R Carcanague
(74) *Attorney, Agent, or Firm* — A. David Joran

(57) ABSTRACT

A compound of formula I:

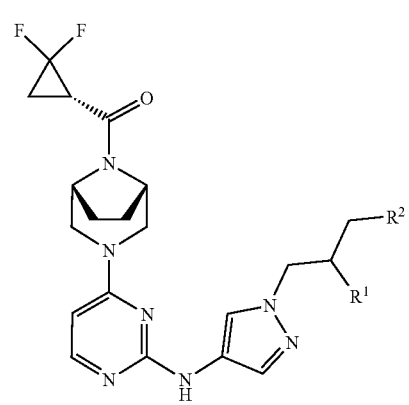

or a pharmaceutically acceptable salt thereof, wherein $R^1$ and $R^2$ are each independently hydrogen or hydroxy; wherein $R^1$ and $R^2$ are not both hydroxy. Also provided are methods of treatment as Janus Kinase inhibitors and pharmaceutical compositions containing the compounds of the invention and combinations thereof with other therapeutic agents.

20 Claims, 2 Drawing Sheets

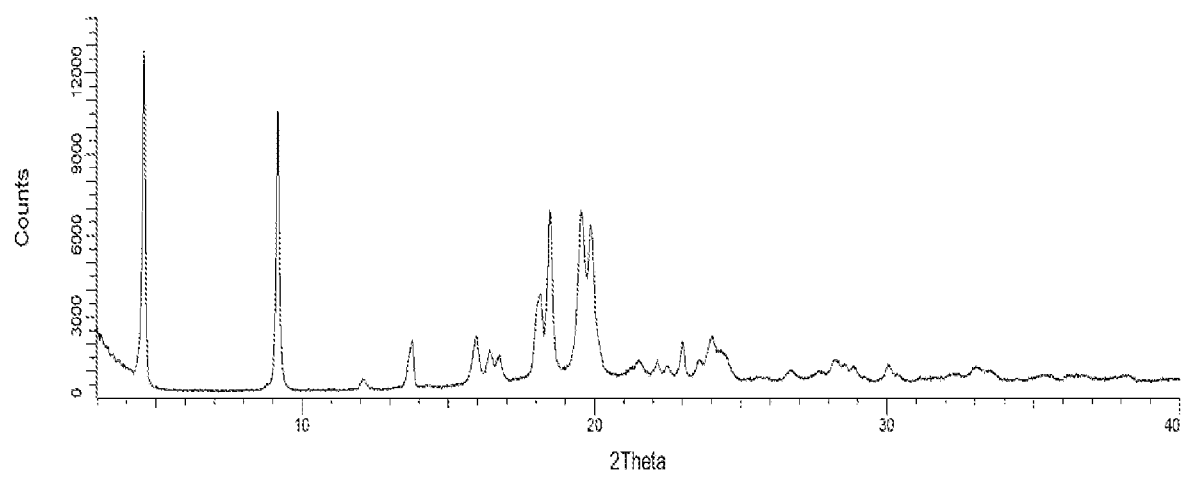

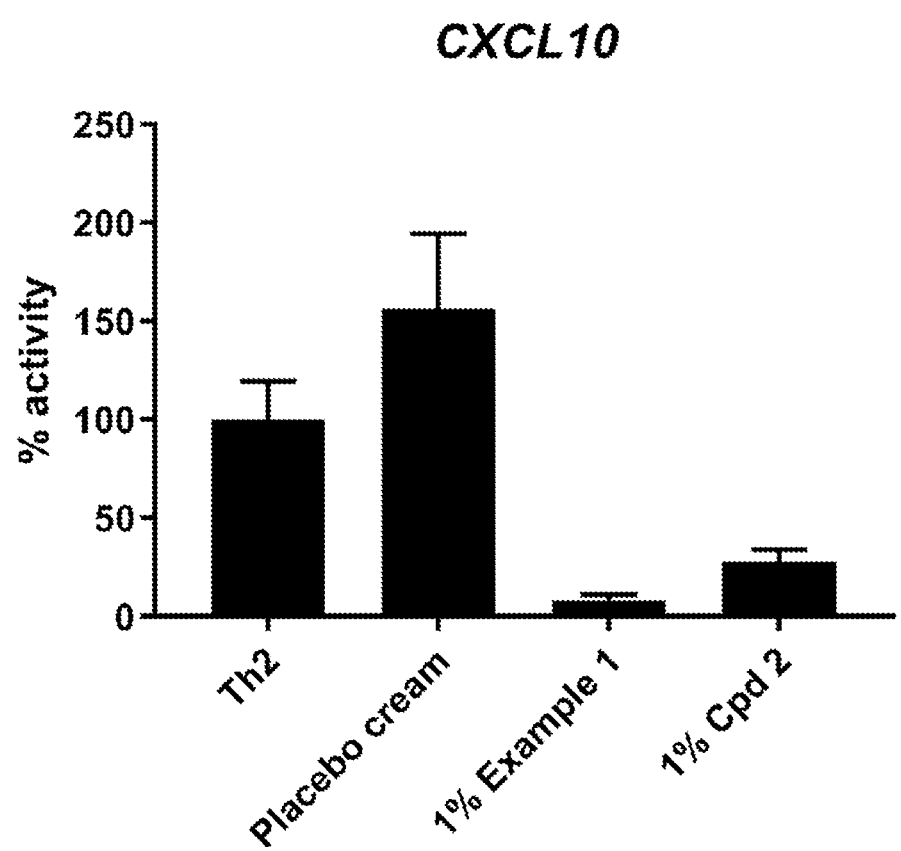

AMINOPYRIMIDINYL DERIVATIVES

FIELD OF THE INVENTION

The present invention provides pharmaceutically active aminopyrimidinyl ligands and analogues. Such compounds are useful for inhibiting Janus Kinases (JAKs). This invention also is directed to compositions comprising said compounds, methods for making such compounds, and methods for treating and preventing conditions mediated by JAKs, and in particular TYK2/JAK1.

BACKGROUND OF THE INVENTION

Protein kinases are families of enzymes that catalyze the phosphorylation of specific residues in proteins, broadly classified into tyrosine and serine/threonine kinases. Inappropriate kinase activity, arising from mutation, over-expression, or inappropriate regulation, dysregulation or deregulation, as well as over- or under-production of growth factors or cytokines has been implicated in many diseases, including but not limited to cancer, cardiovascular diseases, allergies, asthma and other respiratory diseases, autoimmune diseases, inflammatory diseases, bone diseases, metabolic disorders, and neurological and neurodegenerative disorders such as Alzheimer's disease. Inappropriate kinase activity triggers a variety of biological cellular responses relating to cell growth, cell differentiation, cell function, survival, apoptosis, and cell mobility implicated in the aforementioned and related diseases.

Thus, protein kinases have emerged as an important class of enzymes as targets for therapeutic intervention. In particular, the JAK family of cellular protein tyrosine kinases (JAK1, JAK2, JAK3, and TYK2) play a central role in cytokine signaling (Kisseleva et al., *Gene*, 2002, 285, 1; Yamaoka et al. *Genome Biology* 2004, 5, 253). Upon binding to their receptors, cytokines activate JAKs which then phosphorylate the cytokine receptor, thereby creating docking sites for signaling molecules, notably, members of the signal transducer and activator of transcription (STAT) family that ultimately lead to gene expression. Numerous cytokines are known to activate the JAK family. These cytokines include, the interferon (IFN) family (IFN-alpha, IFN-beta, IFN-omega, Limitin, IFN-gamma, IL-10, IL-19, IL-20, IL-22), the gp130 family (IL-6, IL-11, OSM, LIF, CNTF, NNT-1/BSF-3, G-CSF, CT-1, Leptin, IL-12, IL-23), gamma C family (IL-2, IL-7, TSLP, IL-9, IL-15, IL-21, IL-4, IL-13), IL-3 family (IL-3, IL-5, GM-CSF), single chain family (EPO, GH, PRL, TPO), receptor tyrosine kinases (EGF, PDGF, CSF-1, HGF), and G-protein coupled receptors (AT1).

There remains a need for new compounds that effectively and selectively inhibit specific JAK enzymes. JAK enzymes have been shown to be important in the differentiation and function of multiple cell types important in inflammatory disease and autoimmune disease including natural killer cells, B cells, and T helper cell types. Aberrant JAK expression is associated with multiple autoimmune or inflammatory conditions. Modulation of immune activity through inhibition of JAK kinase activity can prove useful in the treatment of various immune disorders (O'Shea J J, Plenge R, *Immunity*, 36, 542-50 (2012); Murray, P. J., *J. Immunol.*, 178, 2623-2629 (2007); Kisseleva, T., et al., *Gene*, 285, 1-24 (2002)).

JAK inhibitors known in the art often have properties which render them generally better suited for oral administration and less well suited for topical administration. Accordingly, the present invention provides novel JAK inhibitors which are both potent JAK inhibitors, and in particular TYK2/JAK1 inhibitors, but also display high clearance in human hepatocytes, thus affording significantly improved systemic clearance, and thereby reducing the risk of adverse side effects upon topical administration while retaining efficacy in the skin.

SUMMARY OF THE INVENTION

The present invention provides a compound having the structure of formula I:

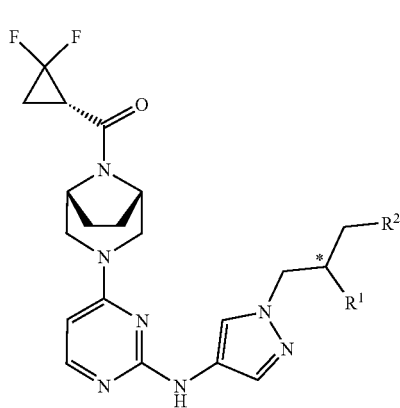

or a pharmaceutically acceptable salt thereof, wherein $R^1$ and $R^2$ are each independently hydrogen or hydroxy; wherein $R^1$ and $R^2$ are not both hydroxy.

In other aspects, the present invention also provides:

pharmaceutical compositions comprising a pharmaceutically acceptable carrier and a compound of formula I, or a pharmaceutically acceptable salt thereof.

In other aspects, the present invention also provides methods for treating conditions or disorders including:

Arthritis, including rheumatoid arthritis, juvenile arthritis, and psoriatic arthritis;

Autoimmune or inflammatory diseases or disorders, including Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, autoimmune hepatitis, primary sclerosing cholangitis, chronic aggressive hepatitis, non-alcoholic fatty liver disease, non-alcoholic steatohepatitis ulcerative colitis and membranous glomerulopathy, systemic lupus erythematosus, rheumatoid arthritis, psoriatic arthritis, Sjogren's syndrome, Reiter's syndrome, polymyositis, dermatomyositis, type I interferonopathies including Aicardi-Goutières syndrome and other mendelian diseases of overexpression of type I interferon systemic sclerosis, polyarteritis nodosa, multiple sclerosis, relapsing remitting multiple sclerosis, primary progressive multiple sclerosis, secondary progressive multiple sclerosis, and bullous pemphigoid, and additional autoimmune diseases, which can be O-cell (humoral) based or T-cell based, including Cogan's syndrome, ankylosing spondylitis, Wegener's granulomatosis, autoimmune alopecia, Type I or juvenile onset diabetes, or thyroiditis;

Cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma, leukemia, including acute myelogenous leukemia and chronic myelogenous leukemia, kidney cancer, lung cancer, muscle cancer, bone cancer, bladder cancer, brain cancer, melanoma including oral and metastatic melanoma, Kaposi's sarcoma, myelomas including multiple myeloma, myeloproliferative disorders, proliferative diabetic retinopathy, or angiogenic-associated disorders including solid tumors;

Diabetes, including Type I diabetes or complications from diabetes;

Eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, or ocular neovascularization;

Intestinal inflammations, including Crohn's disease, ulcerative colitis, inflammatory bowel disease, celiac diseases, proctitis, eosinophilic gastroenteritis, or mastocytosis;

Neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemia, renal ischemia, heart attacks, cardiac hypertrophy, atherosclerosis and arteriosclerosis, organ hypoxia, or platelet aggregation;

Skin diseases, conditions or disorders including atopic dermatitis, hand dermatitis, contact dermatitis, allergic contact dermatitis, irritant contact dermatitis, neurodermatitis, perioral dermatitis, stasis dermatitis, dyshidrotic eczema, xerotic dermatitis, nummular dermatitis, seborrheic dermatitis, eyelid dermatitis, diaper dermatitis, dermatomyositis, lichen planus, lichen sclerosis, alopecia areata, vitiligo, rosacea, epidermolysis bullosa, keratosis pilaris, pityriasis alba, pemphigus, vulvovaginitis, acne, chronic spontaneous urticaria, chronic idiopathic urticaria, chronic physical urticaria, vogt-koyanagi-harada disease, Sutton nevus/nevi, post inflammatory hypopigmentation, senile leukoderma, chemical/drug-induced leukoderma, cutaneous lupus erythematosus, discoid lupus, palmoplantar pustulosis, pemphigoid, sweet's syndrome, hidradenitis suppurativa, psoriasis, plaque psoriasis, pustular psoriasis, nail psoriasis, flexural psoriasis, guttate psoriasis, psoriatic arthritis, erythrodermic psoriasis, or inverse psoriasis;

Allergic reactions including allergic dermatitis in mammal (including horse allergic diseases such as bite hypersensitivity), summer eczema, sweet itch in horses, heaves, inflammatory airway disease, recurrent airway obstruction, airway hyper-responsiveness, or chronic obstruction pulmonary disease;

Asthma and other obstructive airways diseases, including chronic or inveterate asthma, late asthma, bronchitis, bronchial asthma, allergic asthma, intrinsic asthma, extrinsic asthma, or dust asthma; and, Transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, or xeno transplantation.

The present invention will be further understood from the following description given by way of example only. The present invention is directed to a class of aminopyrimidinyl derivatives. In particular, the present invention is directed to aminopyrimidinyl compounds useful as inhibitors of JAKs. While the present invention is not so limited, an appreciation of various aspects of the invention will be gained through the following discussion and the examples.

The terms "isolated" and "in isolated form" means that a compound, or salt thereof, for a compound refers to the physical state of the compound after being isolated from a synthetic process, e.g., from a reaction mixture. Thus the terms "isolated" and "in isolated form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan. As examples, the purification techniques disclosed herein (e.g., LC-MS and LC-MS/MS techniques) result in isolated forms of the subject compounds. Such isolation and purification techniques would be expected to result in product purities containing at least about 70%, at least about 80%, at least about 90%, at least about 95%, at least about 97%, or at least about 99% by weight of the compound, or salt thereof.

The term "subject" refers to a mammal, e.g., human, livestock or companion animals. A "patient", an "individual" or a "subject," used interchangeably, is a mammal, more preferably, a human.

The term "companion animal" or "companion animals" refers to animals kept as pets or household animals. Examples of companion animals include dogs, cats, and rodents including hamsters, guinea pigs, gerbils and the like, rabbits, ferrets and birds.

The term "livestock" refers to animals reared or raised in an agricultural setting to make products such as food or fiber, or for its labor. In some embodiments, livestock are suitable for consumption by mammals, for example humans. Examples of livestock animals include cattle, goats, horses, pigs, sheep, including lambs, and rabbits, as well as birds, such as chickens, ducks and turkeys.

Unless otherwise defined herein, scientific and technical terms used in connection with the present invention have the meanings that are commonly understood by those of ordinary skill in the art.

If substituents are described as being "independently selected" from a group, each substituent is selected independent of the other. Each substituent therefore may be identical to or different from the other substituent(s).

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as "treating" is defined immediately above.

The term "selective", when used herein to describe a functionally-defined receptor ligand or enzyme inhibitor means selective for the defined receptor or enzyme subtype as compared with other receptor or enzyme subtypes in the same family. For instance, a selective TYK2/JAK1 inhibitor is a compound which inhibits the TYK2/JAK1 enzyme subtype more potently than any other JAK enzyme subtype. Such selectivity is, in one embodiment, at least 2 fold (as measured using conventional binding assays), or, in another embodiment, at least 10 fold, or, in a further embodiment, at least 100 fold.

The term "therapeutically-effective" indicates the capability of an agent to prevent, or reduce the severity of, the disorder. The phrase "therapeutically-effective" is to be understood to be equivalent to the phrase "effective for the treatment, prevention, or amelioration", and both are intended to qualify the amount of an agent—which will achieve the goal of mitigating the severity of cancer, cardiovascular disease, or pain and inflammation and the frequency of incidence over treatment of each agent by itself.

"Pharmaceutically acceptable" means suitable for use in a subject.

BRIEF DESCRIPTION OF THE DRAWINGS

FIG. 1 provides a powder X-ray diffraction pattern obtained for crystalline ((S)-2,2-difluorocyclopropyl)((1R, 5S)-3-(2-((1-propyl-1H-pyrazol-4-yl)amino)pyrimidin-4-yl)-3,8-diazabicyclo[3.2.1]octan-8-yl)methanone and Table 1 hereinbelow lists the diffraction peaks in terms of 2-theta values.

FIG. 2 provides the percent change in CXCL10 biomarker after topical administration of 1% formulation of Example 1 and Compound 2 in the Th2 stimulated ex vivo human skin assay in accordance with the disclosure set forth below.

DETAILED DESCRIPTION OF THE INVENTION

The present invention relates to novel compounds which are JAK modulators useful for the treatment of diseases and conditions associated with dysregulation of JAK, in particular, TYK2/JAK1. The present invention further provides pharmaceutical compositions comprising such JAK enzyme modulators as well as methods of treating and/or preventing such diseases and conditions.

According to a first aspect of the invention there is provided a compound of formula I:

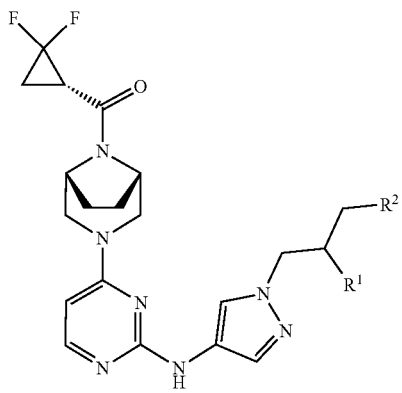

I or a pharmaceutically acceptable salt thereof, wherein $R^1$ and $R^2$ are each independently hydrogen or hydroxy; wherein $R^1$ and $R^2$ are not both hydroxy. Described below are a number of embodiments (E) of this first aspect of the invention, where for convenience E1 is identical thereto.

E1 A compound of formula I as defined above, or a pharmaceutically acceptable salt thereof.

E2. The compound according to E1 or a pharmaceutically acceptable salt thereof, wherein $R^1$ is hydroxy and $R^2$ is hydrogen.

E3. The compound according to E1 or a pharmaceutically acceptable salt thereof, wherein $R^1$ is hydrogen and $R^2$ is hydroxy.

E4. A compound according to E1 of formula IA:

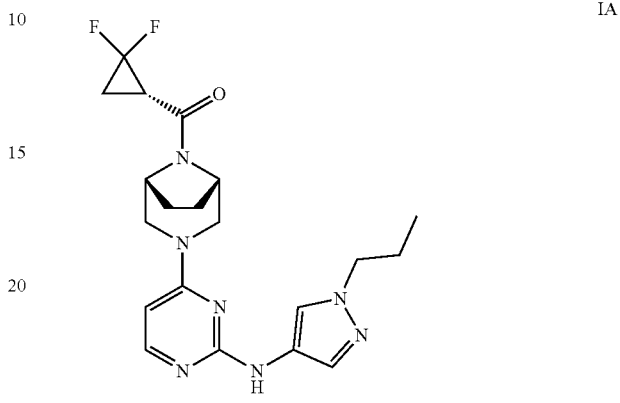

IA or a pharmaceutically acceptable salt thereof.

E5. A compound according to E1 of formula IB:

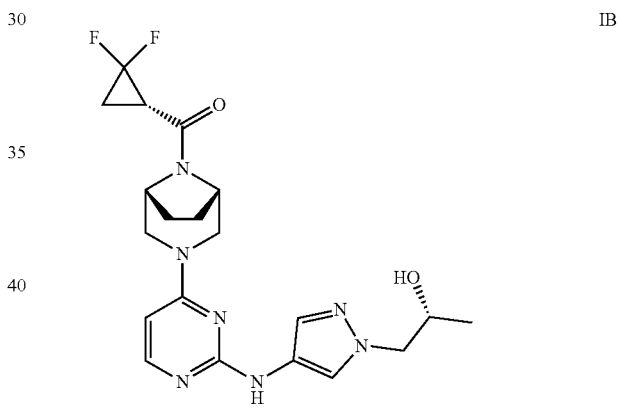

IB or a pharmaceutically acceptable salt thereof.

E6. A compound according to E1 of formula IC:

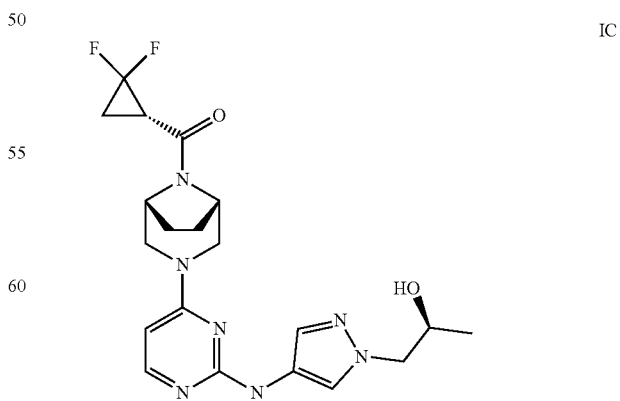

IC or a pharmaceutically acceptable salt thereof.

E7. A compound according to E1 of formula ID:

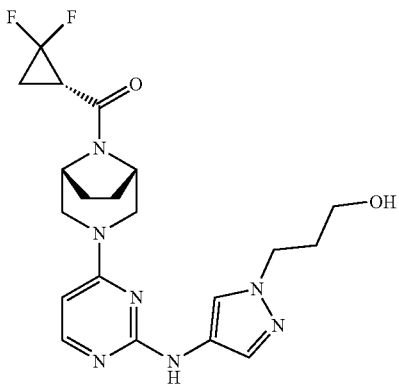

or a pharmaceutically acceptable salt thereof.

E8. A compound according to E1 selected from the group consisting of:
((S)-2,2-Difluorocyclopropyl)((1R,5S)-3-(2-((1-propyl-1H-pyrazol-4-yl)amino)pyrimidin-4-yl)-3,8-diazabicyclo[3.2.1]octan-8-yl)methanone;
((S)-2,2-Difluorocyclopropyl)((1R,5S)-3-(2-((1-((R)-2-hydroxypropyl)-1H-pyrazol-4-yl)amino)pyrimidin-4-yl)-3,8-diazabicyclo[3.2.1]octan-8-yl)methanone;
((S)-2,2-difluorocyclopropyl)((1R,5S)-3-(2-((1-((S)-2-hydroxypropyl)-1H-pyrazol-4-yl)amino)pyrimidin-4-yl)-3,8-diazabicyclo[3.2.1]octan-8-yl)methanone; and,
((S)-2,2-Difluorocyclopropyl)((1R,5S)-3-(2-((1-(3-hydroxypropyl)-1H-pyrazol-4-yl)amino)pyrimidin-4-yl)-3,8-diazabicyclo[3.2.1]octan-8-yl)methanone; or, a pharmaceutically acceptable salt thereof.

E9. ((S)-2,2-Difluorocyclopropyl)((1R,5S)-3-(2-((1-propyl-1H-pyrazol-4-yl)amino)pyrimidin-4-yl)-3,8-diazabicyclo[3.2.1]octan-8-yl)methanone.

E10. ((S)-2,2-Difluorocyclopropyl)((1R,5S)-3-(2-((1-((R)-2-hydroxypropyl)-1H-pyrazol-4-yl)amino)pyrimidin-4-yl)-3,8-diazabicyclo[3.2.1]octan-8-yl)methanone.

E11. ((S)-2,2-Difluorocyclopropyl)((1R,5S)-3-(2-((1-(3-hydroxypropyl)-1H-pyrazol-4-yl)amino)pyrimidin-4-yl)-3,8-diazabicyclo[3.2.1]octan-8-yl)methanone.

E12. ((S)-2,2-difluorocyclopropyl)((1R,5S)-3-(2-((1-((S)-2-hydroxypropyl)-1H-pyrazol-4-yl)amino)pyrimidin-4-yl)-3,8-diazabicyclo[3.2.1]octan-8-yl)methanone.

E13. A compound according to any one of E1 to E12 or a pharmaceutically acceptable salt thereof, in an isolated form.

E14. A compound according to any one of E1 to E13 or a pharmaceutically acceptable salt thereof, in crystalline form.

E15. A pharmaceutical composition comprising a compound according to any one of E1 to E13, or a pharmaceutically acceptable salt thereof, and a pharmaceutically acceptable carrier.

E16. A method of treating or preventing a disease or condition for which a TYK2/JAK1 inhibitor is indicated, in a subject in need of such treatment, comprising administering to the subject a therapeutically effective amount of a compound according to any one of E1 to E14, or a pharmaceutically acceptable salt thereof.

E17. A method of treating or preventing an inflammatory or autoimmune condition comprising administering to a subject in need thereof a therapeutically effective amount of a compound according to any one of E1 to E14, or a pharmaceutically acceptable salt thereof.

E18. A method of treating or preventing a disease or condition selected from inflammation, autoimmune disease, neuroinflammation, arthritis, rheumatoid arthritis, spondyloarthropathies, systemic lupus erythematous, lupus nephritis, osteoarthritis, gouty arthritis, pain, fever, pulmonary sarcoidosis, silicosis, cardiovascular disease, atherosclerosis, myocardial infarction, thrombosis, congestive heart failure and cardiac reperfusion injury, cardiomyopathy, stroke, ischemia, reperfusion injury, brain edema, brain trauma, neurodegeneration, liver disease, inflammatory bowel disease, Crohn's disease, ulcerative colitis, nephritis, retinitis, retinopathy, macular degeneration, glaucoma, diabetes (type 1 and type 2), diabetic neuropathy, viral and bacterial infection, myalgia, endotoxic shock, toxic shock syndrome, osteoporosis, multiple sclerosis, endometriosis, menstrual cramps, vaginitis, candidiasis, cancer, fibrosis, obesity, muscular dystrophy, polymyositis, dermatomyositis, autoimmune hepatitis, primary biliary cirrhosis, primary sclerosing cholangitis, vitiligo, Alzheimer's disease, skin flushing, eczema, psoriasis, atopic dermatitis, sunburn, keloid, hypertrophic scar, rheumatic diseases, urticaria, discoid lupus, cutaneous lupus, central nervous system lupus, psoriatic arthritis, asthma, allergic asthma, type I interferonopathies including Aicardi-Goutieres syndrome and other mendelian diseases of overexpression of type I interferon, primary progressive multiple sclerosis, relapsing remitting multiple sclerosis, non-alcoholic fatty liver disease, non-alcoholic steatohepatitis, scleroderma, alopecia areata, scarring alopecia, prurigo, prurigo nodularis, CPUO, lichen diseases, lichen planus, Steven's Johnson's syndrome, spondylopathy, myositis, vasculitis, pemphigus, lupus, major depression disorder, allergy, dry eye syndrome, transplant rejection, cancer, septic shock, cardiopulmonary dysfunction, acute respiratory disease, ankylosing spondylitis, cachexia, chronic graft-versus-host disease, acute graft-versus-host disease, Celiac Sprue, idiopathic thrombocytopenic thrombotic purpura, thrombotic thrombocytopenic purpura, myasthenia gravis, Sjogren's syndrome, epidermal hyperplasia, cartilage inflammation, bone degradation, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile Reter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, enteropathic arthritis, reactive arthritis, Reter's Syndrome, myolitis, polymyolitis, dermatomyolitis, polyarteritis nodosa, Wegener's granulomatosis, arteritis, polymyalgia rheumatica, sarcoidosis, sclerosis, primary biliary sclerosis, sclerosing cholangitis, dermatitis, Still's disease, chronic obstructive pulmonary disease, Guillain-Barre disease, Graves' disease, Addison's disease, Raynaud's phenomenon, psoriatic epidermal hyperplasia, plaque psoriasis, guttate psoriasis, inverse psoriasis, pustular psoriasis, erythrodermic psoriasis, an immune disorder associated with or arising from activity of pathogenic lymphocytes, noninfectious uveitis, Behcet's disease and Vogt-Koyanagi-Harada syndrome, comprising administering to a subject in need thereof a therapeutically effective amount of a compound according to any one of E1 to E14, or a pharmaceutically acceptable salt thereof.

E19. The method according to any one of E16 to E18 wherein the compound is selected from the group consisting of:
((S)-2,2-Difluorocyclopropyl)((1R,5S)-3-(2-((1-propyl-1H-pyrazol-4-yl)amino)pyrimidin-4-yl)-3,8-diazabicyclo[3.2.1]octan-8-yl)methanone;
((S)-2,2-Difluorocyclopropyl)((1R,5S)-3-(2-((1-((R)-2-hydroxypropyl)-1H-pyrazol-4-yl)amino)pyrimidin-4-yl)-3,8-diazabicyclo[3.2.1]octan-8-yl)methanone;
((S)-2,2-difluorocyclopropyl)((1R,5S)-3-(2-((1-((S)-2-hydroxypropyl)-1H-pyrazol-4-yl)amino)pyrimidin-4-yl)-3,8-diazabicyclo[3.2.1]octan-8-yl)methanone; and,
((S)-2,2-Difluorocyclopropyl)((1R,5S)-3-(2-((1-(3-hydroxypropyl)-1H-pyrazol-4-yl)amino)pyrimidin-4-yl)-3,8-diazabicyclo[3.2.1]octan-8-yl)methanone; or, a pharmaceutically acceptable salt thereof.

E20. The method according to any one of E16 to E18 wherein the compound is ((S)-2,2-difluorocyclopropyl)((1R,5S)-3-(2-((1-propyl-1H-pyrazol-4-yl)amino)pyrimidin-4-yl)-3,8-diazabicyclo[3.2.1]octan-8-yl)methanone; or, a pharmaceutically acceptable salt thereof, in an isolated form.

E21. The method according to any one of E16 to E18 wherein the compound is ((S)-2,2-difluorocyclopropyl)((1R,5S)-3-(2-((1-(3-hydroxypropyl)-1H-pyrazol-4-yl)amino)pyrimidin-4-yl)-3,8-diazabicyclo[3.2.1]octan-8-yl)methanone; or, a pharmaceutically acceptable salt, in an isolated form.

E22. The method according to any one of E16 to E19, wherein the disease or condition is psoriasis.

E23. The method according to any one of E16 to E19, wherein the disease or condition is atopic dermatitis.

E24. The method according to any one of E16 to E19, wherein the disease or condition is hand eczema.

E25. The method according to any one of E16 to E19, wherein the disease or condition is pruritis.

E26. The method according to any one of E16 to E19, wherein the disease or condition is cutaneous lupus.

E27. The method according to any one of E16 to E19, wherein the compound is administered topically.

E28. Use of a compound, or a pharmaceutically acceptable salt thereof, according to any of E1 to E14 for the manufacture of a medicament for the treatment of a disorder for which a TYK2/JAK1 inhibitor is indicated.

E29. A compound, or a pharmaceutically acceptable salt thereof, according to any of E1 to E14 for use in the treatment of a disorder for which a TYK2/JAK1 inhibitor is indicated.

E30. A pharmaceutical combination comprising a compound in isolated form, or a pharmaceutically acceptable salt thereof, of any of E1 to E14, or a pharmaceutically acceptable salt thereof, and one or more additional pharmacologically active compounds.

E40. The compound according to E4 in crystalline form having an X-ray powder diffraction pattern comprising diffraction peaks at 4.6, 9.2, 18.5, and 19.6±0.2° 2θ.

In certain embodiments, the therapeutically effective amount used in accord with the method is from 0.01 mg/kg of body weight/day to 100 mg/kg of body weight/day. In certain other embodiments, the therapeutically effective amount used in accord with the method is wherein the therapeutically effective amount is from 0.1 mg/kg of body weight/day to 10 mg/kg of body weight/day.

In certain embodiment, the present invention provides a topical pharmaceutical formulation comprising an active agent present in a concentration of about 0.0001% to about 10.0% (w/w). In another embodiment, the active agent is present in a concentration of about 0.001% to about 3.0% (w/w). In another embodiment, the active agent is present in a concentration of about 0.01% to about 3.0% (w/w).

Compounds of the invention that have the same molecular formula but differ in the nature or sequence of bonding of their atoms or the arrangement of their atoms in space are termed "isomers". Isomers that differ in the arrangement of their atoms in space are termed "stereoisomers". These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30. The enantiomers of the present invention indicated by (R), (S), or * are substantially free of the other enantiomer. "Substantially free" means that the enantiomeric excess is greater than about 90%, preferably greater than about 95%, and more preferably greater than about 99%. Within the context of enantiomeric excess, the term "about" means ±1.0%. The symbol * designates a chiral carbon atom as either (R) or (S) stereochemistry depending on the configuration of substituents around the chiral carbon atom. The present invention contemplates various stereoisomers and mixtures thereof that are specifically included within the scope of this invention. Stereoisomers include enantiomers and mixtures of enantiomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution include, but are not limited to, (1) attachment of a chiral auxiliary to a mixture of enantiomers, separation of the resulting mixture of diastereomers by recrystallization or chromatography and liberation of the optically pure product from the auxiliary or (2) direct separation of the mixture of optical enantiomers on chiral chromatographic columns. Compounds of the present invention not designated (R), (S), or * may exist as racemates (i.e. 50% (R) and 50% (S)) or as a mixture of two enantiomers wherein one enantiomer is in excess. For example, enantiomeric mixtures may include the (R) enantiomer in 51% and the (S) enantiomer in 49% or vice versa or any combination of (R) and (S) other than the racemic mixture of 50% (R) and 50% (S).

Included within the scope of the described compounds are all isomers (e.g., cis-, trans-, or diastereomers) of the compounds described herein alone as well as any mixtures. All of these forms, including enantiomers, diastereomers, cis, trans, syn, anti, solvates (including hydrates), tautomers, and mixtures thereof, are included in the described compounds. Stereoisomeric mixtures, e.g., mixtures of diastereomers, can be separated into their corresponding isomers in a known manner by means of suitable separation methods. Diastereomeric mixtures for example may be separated into their individual diastereomers by means of fractionated crystallization, chromatography, solvent distribution, and similar procedures. This separation may take place either at the level of one of the starting compounds or in a compound of formula I, IA, IB, IC or ID itself. Enantiomers may be separated through the formation of diastereomeric salts, for example by salt formation with an enantiomer-pure chiral acid, or by means of chromatography, for example by HPLC, using chromatographic substrates with chiral ligands. The present invention includes all pharmaceutically acceptable isotopically-labelled compounds of formula I, IA, IB, IC or ID, or a pharmaceutically acceptable salt thereof, wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of formula I, IA, IB, IC or ID, or a pharmaceutically acceptable salt thereof, for example, those incorporating a radioactive isotope, are useful in drug and/or substrate tissue distribution studies. The radioactive isotopes tritium, i.e., $^3H$, and carbon-14, i.e., $^{14}C$, are particularly useful for this purpose in view of their ease of incorporation and ready means of detection.

Substitution with heavier isotopes such as deuterium, i.e., $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula I, IA, IB, IC or ID can generally be prepared by conventional techniques known to those skilled in the art or by processes analogous to those described in the accompanying Examples and Preparations using an appropriate isotopically-labeled reagent in place of the non-labeled reagent previously employed.

In therapeutic use for treating disorders in a mammal, a compound of the present invention or its pharmaceutical compositions can be administered orally, parenterally, topically, rectally, transmucosally, or intestinally. Parenteral administrations include indirect injections to generate a systemic effect or direct injections to the afflicted area. Topical administrations include the treatment of skin or organs readily accessible by local application, for example, eyes or ears. It also includes transdermal delivery to generate a systemic effect. The rectal administration includes the form of suppositories. The preferred routes of administration are oral and parenteral.

Pharmaceutically acceptable salts of the compound of formula I, IA, IB, IC or ID include the acid addition and base salts thereof. Suitable acid addition salts are formed from acids which form non-toxic salts. Examples include the acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulfate and hemicalcium salts. For a review on suitable salts, see Handbook of Pharmaceutical Salts: Properties, Selection, and Use by Stahl and Wermuth (Wiley-VCH, 2002).

Pharmaceutically acceptable salts of a compound of formula I, IA, IB, IC or ID may be prepared, respectively, by one or more of three methods: (i) by reacting the compound of formula I, IA, IB, IC or ID with the desired acid; (ii) by removing an acid- or base-labile protecting group from a suitable precursor of a compound of formula I, IA, IB, IC or ID, or by ring-opening a suitable cyclic precursor, for example, a lactone or lactam, using the desired acid or base; or (iii) by converting one salt of a compound of formula I, IA, IB, IC or ID to another by reaction with an appropriate acid or base or by means of a suitable ion exchange column. All three reactions are typically carried out in solution. The resulting salt may precipitate out and be collected by filtration or may be recovered by evaporation of the solvent. The degree of ionization in the resulting salt may vary from completely ionized to almost non-ionized.

The invention also includes the following embodiments:
a compound of I, IA, IB, IC or ID, or a pharmaceutically acceptable salt thereof, as defined in any of the embodiments described herein, for use as a medicament;
a compound of 1, IA, IB, IC or ID, or a pharmaceutically acceptable salt thereof, as defined in any of the embodiments described herein, for use in the treatment of selected from inflammation, autoimmune disease, neuroinflammation, arthritis, rheumatoid arthritis, spondyloarthropathies, systemic lupus erythematous, lupus nephritis, osteoarthritis, gouty arthritis, pain, fever, pulmonary sarcoidosis, silicosis, cardiovascular disease, atherosclerosis, myocardial infarction, thrombosis, congestive heart failure and cardiac reperfusion injury, cardiomyopathy, stroke, ischemia, reperfusion injury, brain edema, brain trauma, neurodegeneration, liver disease, inflammatory bowel disease, Crohn's disease, ulcerative colitis, nephritis, retinitis, retinopathy, macular degeneration, glaucoma, diabetes (type 1 and type 2), diabetic neuropathy, viral and bacterial infection, myalgia, endotoxic shock, toxic shock syndrome, osteoporosis, multiple sclerosis, endometriosis, menstrual cramps, vaginitis, candidiasis, cancer, fibrosis, obesity, muscular dystrophy, polymyositis, dermatomyositis, autoimmune hepatitis, primary biliary cirrhosis, primary sclerosing cholangitis, vitiligo, Alzheimer's disease, skin flushing, eczema, psoriasis, atopic dermatitis, sunburn, keloid, hypertrophic scar, rheumatic diseases, urticaria, discoid lupus, cutaneous lupus, central nervous system lupus, psoriatic arthritis, asthma, allergic asthma, type I interferonopathies including Aicardi-Goutieres syndrome and other mendelian diseases of overexpression of type I interferon, primary progressive multiple sclerosis, relapsing remitting multiple sclerosis, non-alcoholic fatty liver disease, non-alcoholic steatohepatitis, scleroderma, alopecia areata, spondylopathy, myositis, vasculitis, pemphigus, lupus, major depression disorder, allergy, dry eye syndrome, transplant rejection, cancer, septic shock, cardiopulmonary dysfunction, acute respiratory disease, ankylosing spondylitis, cachexia, chronic graft-versus-host disease, acute graft-versus-host disease, Celiac Sprue, idiopathic thrombocytopenic thrombotic purpura, myasthenia gravis, Sjogren's syndrome, epidermal hyperplasia, cartilage inflammation, bone degradation, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile Reter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, enteropathic arthritis, reactive arthritis, Reter's Syndrome, myolitis, polymyolitis, dermatomyolitis, polyarteritis nodosa, Wegener's granulomatosis, arteritis, polymyalgia rheumatica, sarcoidosis, sclerosis, primary biliary sclerosis, sclerosing cholangitis, dermatitis, Still's disease, chronic obstructive pulmonary disease, Guillain-Barre disease, Graves' disease, Addison's disease, Raynaud's phenomenon, psoriatic epidermal hyperplasia, plaque psoriasis, guttate psoriasis, inverse psoriasis, pustular psoriasis, erythrodermic psoriasis, an immune disorder associated with or arising from activity of pathogenic lymphocytes, noninfectious uveitis, Behcet's disease or Vogt-Koyanagi-Harada syndrome;

a method of treating a disease for which an inhibitor of JAK is indicated, in a subject in need of such treatment, comprising administering to the subject a therapeutically effective amount of a compound of formula I, IA, IB, IC or ID, or a pharmaceutically acceptable salt thereof, as defined in any of the embodiments described herein;

the use of a compound of formula I, IA, IB, IC or ID, or a pharmaceutically acceptable salt thereof, as defined in any of the embodiments described herein, for the manufacture of a medicament for treating a disease or condition for which an inhibitor of JAK is indicated;

a compound of formula I, IA, IB, IC or ID, or a pharmaceutically acceptable salt thereof, as defined in any of the embodiments described herein, for use in the treatment of a disease or condition for which an inhibitor of JAK is indicated;

a pharmaceutical composition for the treatment of a disease or condition for which an inhibitor of JAK is indicated, comprising a compound of formula I, IA, IB, IC or ID, or a pharmaceutically acceptable salt thereof, as defined in any of the embodiments described herein.

The present invention also provides any of the uses, methods or compositions as defined above wherein the compound of formula I, IA, IB, IC or ID, or a pharmaceutically acceptable salt thereof, is used in combination with another pharmacologically active compound, particularly one of the functionally-defined classes or specific compounds listed below. These agents may be administered as part of the same or separate dosage forms, via the same or different routes of administration, and on the same or different administration schedules according to standard pharmaceutical practice known to one skilled in the art.

Suitable agents for use in combination therapy with a compound of formula I, IA, IB, IC or ID, or a pharmaceutically acceptable salt thereof, sulfasalazine, mesalazine, prednisone, azathioprine, infliximab, adalimumab, belimumab, becertolizumab, natalizumab, vedolizumab, hydrocortisone, budesonide, cyclosporin, tacrolimus, fexofenadine, 6-mercaptopurine, methotrexate, ursodeoxycholic acid, obeticholic acid, anti-histamines, rifampin, prednisone, methotrexate, azathioprine, cyclophosphamide, hydroxychloroquine, mofetil, sodium mycophenolate, tacrolimus, leflunomide, chloroquine and quinacrine, thalidomide, rituxan, NSAIDs, solumedrol, depomedrol and dexamethasone.

Other suitable agents for use in combination therapy with a compound of formula I, IA, IB, IC or ID, or a pharmaceutically acceptable salt thereof, include: a 5-lipoxygenase activating protein (FLAP) antagonist; a leukotriene antagonist (LTRA) such as an antagonist of $LTB_4$, $LTC_4$, $LTD_4$, $LTE_4$, $CysLT_1$ or $CysLT_2$, e.g., montelukast or zafirlukast; a histamine receptor antagonist, such as a histamine type 1 receptor antagonist or a histamine type 2 receptor antagonist, e.g., loratidine, fexofenadine, desloratidine, levocetirizine, methapyrilene or cetirizine; an α1-adrenoceptor agonist or an α2-adrenoceptor agonist, e.g., phenylephrine, methoxamine, oxymetazoline or methylnorephrine; a muscarinic M3 receptor antagonist, e.g., tiotropium or ipratropium; a dual muscarinic M3 receptor antagononist/β2 agonist; a PDE inhibitor, such as a PDE3 inhibitor, a PDE4 inhibitor or a PDE5 inhibitor, e.g., theophylline, sildenafil, vardenafil, tadalafil, ibudilast, cilomilast or roflumilast; sodium cromoglycate or sodium nedocromil; a cyclooxygenase (COX) inhibitor, such as a non-selective inhibitor (e.g., aspirin or ibuprofen) or a selective inhibitor (e.g., celecoxib or valdecoxib); a glucocorticosteroid, e.g., fluticasone, mometasone, dexamethasone, prednisolone, budesonide, ciclesonide or beclamethasone; an anti-inflammatory monoclonal antibody, e.g., infliximab, adalimumab, tanezumab, ranibizumab, bevacizumab or mepolizumab; a β2 agonist, e.g., salmeterol, albuterol, salbutamol, fenoterol or formoterol, particularly a long-acting β2 agonist; an integrin antagonist, e.g., natalizumab; an adhesion molecule inhibitor, such as a VLA-4 antagonist; a kinin $B_1$ or $B_2$ receptor antagonist; an immunosuppressive agent, such as an inhibitor of the IgE pathway (e.g., omalizumab) or cyclosporine; a matrix metalloprotease (MMP) inhibitor, such as an inhibitor of MMP-9 or MMP-12; a tachykinin $NK_1$, $NK_2$ or $NK_3$ receptor antagonist; a protease inhibitor, such as an inhibitor of elastase, chymase or catheopsin G; an adenosine $A_{2a}$ receptor agonist; an adenosine $A_{2b}$ receptor antagonist; a urokinase inhibitor; a dopamine receptor agonist (e.g., ropinirole), particularly a dopamine D2 receptor agonist (e.g., bromocriptine); a modulator of the NFκB pathway, such as an IKK inhibitor; a further modulator of a cytokine signalling pathway such as an inhibitor of JAK kinase, syk kinase, p38 kinase, SPHK-1 kinase, Rho kinase, EGF-R or MK-2; a mucolytic, mucokinetic or anti-tussive agent; an antibiotic; an antiviral agent; a vaccine; a chemokine; an epithelial sodium channel (ENaC) blocker or Epithelial sodium channel (ENaC) inhibitor; a nucleotide receptor agonist, such as a P2Y2 agonist; a thromboxane inhibitor; niacin; a 5-lipoxygenase (5-LO) inhibitor, e.g., Zileuton; an adhesion factor, such as VLAM, ICAM or ELAM; a CRTH2 receptor ($DP_2$) antagonist; a prostaglandin $D_2$ receptor ($DP_1$) antagonist; a haematopoietic prostaglandin D2 synthase (HPGDS) inhibitor; interferon-β; a soluble human TNF receptor, e.g., Etanercept; a HDAC inhibitor; a phosphoinositotide 3-kinase gamma (PI3Kγ) inhibitor; a phosphoinositide 3-kinase delta (PI3Kδ) inhibitor; a CXCR-1 or a CXCR-2 receptor antagonist; an IRAK-4 inhibitor; and, a TLR-4 or TLR-9 inhibitor, including the pharmaceutically acceptable salts of the specifically named compounds. The agents may be administered with another active agent, wherein the second active agent may be administered either orally or topically.

Accordingly, the invention provides methods of treating or preventing a disease, condition or disorder associated with JAK in a subject, such as a human or non-human mammal, comprising administering an effective amount of one or more compounds described herein to the subject in need thereof. Conditions in which selective targeting of the JAK pathway or modulation of the JAK kinases are contemplated to be therapeutically useful include, inter alia, arthritis, asthma, autoimmune diseases, cancers or tumors, diabetes, certain eye diseases, disorders or conditions, inflammation, intestinal inflammations, allergies or conditions, neurodegenerative diseases, psoriasis, and transplant rejection.

One way of carrying out the invention is to administer a compound of formula I, IA, IB, IC or ID in the form of a prodrug. Thus, certain derivatives of a compound of formula I, IA, IB, IC or ID which may have little or no pharmacological activity themselves can, when administered into or onto the body, be converted into a compound of formula I, IA, IB, IC or ID having the desired activity, for example by hydrolytic cleavage, particularly hydrolytic cleavage promoted by an esterase or peptidase enzyme. Such derivatives are referred to as "prodrugs." Further information on the use of prodrugs may be found in 'Pro-drugs as Novel Delivery Systems', Vol. 14, *ACS Symposium Series* (T. Higuchi and W. Stella) and 'Bioreversible Carriers in Drug Design', Pergamon Press, 1987 (Ed. E. B. Roche, American Pharmaceutical Association). Reference can also be made to *Nature Reviews/Drug Discovery*, 2008, 7, 355 and *Current Opinion in Drug Discovery and Development*, 2007, 10, 550.

Prodrugs in accordance with the invention can, for example, be produced by replacing appropriate functionalities present in the compounds of formula I, IA, IB, IC or ID with certain moieties known to those skilled in the art as 'pro-moieties' as described, for example, in 'Design of Prodrugs' by H. Bundgaard (Elsevier, 1985).

Thus, a prodrug in accordance with the invention is (a) an ester or amide derivative of a hydroxy group in a compound of formula I, IA, IB, IC or ID; (b) an ester, carbonate, carbamate, phosphate or ether derivative of a hydroxy group in a compound of formula I, IA, IB, IC or ID; (c) an amide, imine, carbamate or amine derivative of an amino group in a compound form formula I, IA, IB, IC or ID; (d) an oxime or imine derivative of a carbonyl group in a compound of formula I, IA, IB, IC or ID.

Some specific examples of prodrugs in accordance with the invention include:
(i) where the compound of formula I, IA, IB, IC or ID contains a hydroxyl functionality
(ii) where the compound of formula I, IA, IB, IC or ID contains an alcohol functionality (—OH), an ester thereof, such as a compound wherein the hydrogen of the alcohol functionality of the compound of formula I, IA, IB, IC or ID is replaced by —CO($C_1$-$C_8$ alkyl) (e.g., methylcarbonyl) or the alcohol is esterified with an amino acid;
(iii) where the compound of formula I, IA, IB, IC or ID contains an alcohol functionality (—OH), an ether thereof, such as a compound wherein the hydrogen of the alcohol functionality of the compound of formula I, IA, IB, IC or ID is replaced by ($C_1$-$C_8$ alkyl)C(=O)OCH$_2$— or —CH$_2$OP(=O)(OH)$_2$;
(iv) where the compound of formula I, IA, IB, IC or ID contains an alcohol functionality (—OH), a phosphate thereof, such as a compound wherein the hydrogen of the alcohol functionality of the compound of formula I, IA, IB, IC or ID is replaced by —P(=O)(OH)$_2$ or —P(=O)(ONa)$_2$ or —P(=O)(O$^-$)$_2$Ca$^{2+}$;
(v) where the compound of formula I, IA, IB, IC or ID contains a secondary amino functionality (—NHR where R≠H), an amide thereof, for example, a compound wherein, as the case may be, one or both hydrogens of the amino functionality of the compound of formula I, IA, IB, IC or ID is/are replaced by ($C_1$-$C_{10}$)alkanoyl, —COCH$_2$NH$_2$ or the amino group is derivatised with an amino acid;
(vi) where the compound of formula I, IA, IB, IC or ID contains a secondary amino functionality (—NH$_2$ or —NHR where R H), an amine thereof, for example, a compound wherein, as the case may be, one or both hydrogens of the amino functionality of the compound of formula I, IA, IB, IC or ID is/are replaced by —CH$_2$OP(=O)(OH)$_2$.

References to compounds of formula I, IA, IB, IC or ID are taken to include the compounds themselves and prodrugs thereof. The invention includes such compounds of formula I, IA, IB, IC or ID as well as pharmaceutically acceptable salts of such compounds.

Also included within the scope of the invention are active metabolites of compounds of formula I, IA, IB, IC or ID, that is, compounds formed in vivo upon administration of the drug, often by oxidation or dealkylation. Some examples of metabolites in accordance with the invention include
(i) where the compound of formula I, IA, IB, IC or ID contains a methylene group, an hydroxymethylene derivative thereof (—CH$_2$—→—CHOH):
(ii) where the compound of formula I, IA, IB, IC or ID contains a tertiary amino group, a secondary amino derivative thereof (—NRR'→—NHR or —NHR'); and,
(iii) where the compound of formula I, IA, IB, IC or ID contains a secondary amino group, a primary derivative thereof (—NHR→—NH$_2$).

Pharmaceutical Compositions or Formulations

In another embodiment, the present invention provides pharmaceutical compositions, or formulations, comprising a therapeutically effective amount of a compound of the present invention and a pharmaceutically acceptable diluent or carrier. The pharmaceutical compositions, or formulations, of this invention may be administered to humans and other mammals topically, orally, parenterally, intracisternally, intravaginally, intraperitoneally, buccally, as an oral spray, as a nasal spray, rectally as a suppository, or in the form of a liposome.

A typical pharmaceutical composition or formulation is prepared by mixing a compound of the present invention and a carrier or diluent. Suitable carriers and diluents include materials such as carbohydrates, waxes, water soluble and/or swellable polymers, hydrophilic or hydrophobic materials, gelatin, oils, solvents, water, and the like. The particular carrier or diluent used will depend upon the means and purpose for which the compound of the present invention is being applied. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., for use in the preparing a medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the carriers described above. The dissolution rate of poorly water-soluble compounds may be enhanced by the use of a spray-dried dispersion, such as those described by Takeuchi, H., et al., in "Enhancement of the dissolution rate of a poorly water-soluble drug (tolbutamide) by a spray-drying solvent deposition method and disintegrants," *J. Pharm. Pharmacol.*, 39, 769-773 (1987); and EP0901786 B1 (US2002/009494), incorporated herein by reference. The compound of the present invention is typically formulated into pharmaceutical dosage forms to provide an easily controllable dosage of the drug and to give the patient an elegant and easily handleable product.

The pharmaceutical composition, or formulation, for application may be packaged in a variety of ways depending upon the method used for administering the drug. Generally, an article for distribution includes a container having deposited therein the pharmaceutical formulation in an appropriate form. Suitable containers include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The term "pharmaceutically acceptable carrier" refers to carrier medium that provides the appropriate delivery of an effective amount of an active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Additional information concerning carriers can be found in Remington: The Science and Practice of Pharmacy, 21st Ed., Lippincott, Williams & Wilkins (2005) which is incorporated herein by reference. Further examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; carriers such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The term "pharmaceutically acceptable topical carrier" refers to pharmaceutically acceptable carriers, as described herein above, suitable for topical application. An inactive liquid or cream vehicle capable of suspending or dissolving the active agent(s), and having the properties of being nontoxic and non-inflammatory when applied to the skin, nail, hair, claw or hoof is an example of a pharmaceutically-acceptable topical carrier. This term is specifically intended to encompass carrier materials approved for use in topical cosmetics as well.

The term "topical administration" refers to the application of a pharmaceutical agent to the external surface of the skin, nail, hair, claw or hoof, such that the agent crosses the external surface of the skin, nail, hair, claw or hoof and enters the underlying tissues. Topical administration includes application of the composition to intact skin, nail, hair, claw or hoof, or to a broken, raw or open wound of skin, nail, hair, claw or hoof. Topical administration of a pharmaceutical agent can result in a limited distribution of the agent to the skin and surrounding tissues or, when the agent is removed from the treatment area by the bloodstream, can result in systemic distribution of the agent.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Compounds that are volatile in may require admixture with special formulating agents or with special packaging materials to assure proper dosage delivery. In addition, compounds of the present invention that have poor human skin permeability may require one or more permeability enhancers whereas compounds rapidly absorbed through the skin may require formulation with absorption-retarding agents or barriers.

The ointments, pastes, creams, lotions, gels, powders, and solutions, for topical administration may contain, in addition to an active compound of the present invention, pharmaceutically acceptable carriers such as animal and vegetable fats, oils, waxes, paraffins, starch, tragacanth, cellulose derivatives, polyethylene glycols, silicones, bentonites, silicic acid, talc, zinc oxide, preservatives, antioxidants, fragrances, emulsifiers, dyes, inert fillers, anti-irritants, tackifiers, fragrances, opacifiers, antioxidants, gelling agents, stabilizers, surfactants, emollients, coloring agents, preservatives, buffering agents, permeation enhancers, or mixtures thereof. Topical carriers should not interfere with the effectiveness of the biological activity of the active agent and not be deleterious to the epithelial cells or their function.

The terms "permeability enhancer," or "permeation enhancer," relates to an increase in the permeability of the skin, nail, hair, claw or hoof to a drug, so as to increase the rate at which the drug permeates through the skin, nail, hair, claw or hoof. The enhanced permeation effected through the use of such enhancers can be observed, for example, by measuring the rate of diffusion of the drug through animal or human skin, nail, hair, claw or hoof using a diffusion cell apparatus. A diffusion cell is described by Merritt et al. Diffusion Apparatus for Skin Penetration, J of Controlled Release, 1 (1984) pp. 161-162. The term "permeation enhancer" or "penetration enhancer" intends an agent or a mixture of agents, which, alone or in combination, act to increase the permeability of the skin, nail, hair or hoof to a drug.

The term "transdermal delivery" refers to the diffusion of an agent across the barrier of the skin, nail, hair, claw or hoof resulting from topical administration or other application of a composition. The stratum corneum acts as a barrier and few pharmaceutical agents are able to penetrate intact skin. In contrast, the epidermis and dermis are permeable to many solutes and absorption of drugs therefore occurs more readily through skin, nail, hair, claw or hoof that is abraded or otherwise stripped of the stratum corneum to expose the epidermis. Transdermal delivery includes injection or other delivery through any portion of the skin, nail, hair, claw or hoof or mucous membrane and absorption or permeation through the remaining portion. Absorption through intact skin, nail, hair, claw or hoof can be enhanced by placing the active agent in an appropriate pharmaceutically acceptable vehicle before application to the skin, nail, hair, claw or hoof. Passive topical administration may consist of applying the active agent directly to the treatment site in combination with emollients or penetration enhancers. As used herein, transdermal delivery is intended to include delivery by permeation through or past the integument, i.e. skin, nail, hair, claw or hoof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Solid dosage forms for oral administration include capsules, tablets, pills, powders, and granules. In such solid dosage forms, the active compound is mixed with at least one inert pharmaceutically acceptable carrier such as sodium citrate or calcium phosphate and/or a) fillers or extenders such as starches, lactose, sucrose, glucose, mannitol, and salicylic acid; b) binders such as carboxymethylcellulose, alginates, gelatin, polyvinyl pyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions which can be used include polymeric substances and waxes.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

The term "parenterally," as used herein, refers to modes of administration which include intravenous, intramuscular, intraperitoneal, intrasternal, subcutaneous, intraarticular injection and infusion. Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

Pharmaceutical compositions, or formulations, for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Compounds of the present invention may also be administered in the form of liposomes. Liposomes are generally derived from phospholipids or other lipid substances and are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, and the like. The preferred lipids are the natural and synthetic phospholipids and phosphatidylcholines (lecithins) used separately or together. Methods to form liposomes are known in the art. See, for example, Prescott, Ed., Methods in Cell Biology, Volume XIV, Academic Press, New York, N.Y. (1976), p 33 et seq.

Pharmaceutical compositions, or formulations, of the present invention may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

The pharmaceutical compositions, or formulations, of the invention may be suspensions. Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

The pharmaceutical compositions also include solvates and hydrates of the compounds of the present invention. The term "solvate" refers to a molecular complex of a compound represented by Formula I, IA, IB, IC or ID, including pharmaceutically acceptable salts thereof, with one or more solvent molecules. Such solvent molecules are those commonly used in the pharmaceutical art, which are known to be innocuous to the recipient, e.g., water, ethanol, ethylene glycol, (S)-propylene glycol, (R)-propylene glycol, and the like, The term "hydrate" refers to the complex where the solvent molecule is water. The solvates and/or hydrates preferably exist in crystalline form. Other solvents may be used as intermediate solvates in the preparation of more desirable solvates. Intermediate solvents include, but are not limited to, methanol, methyl t-butyl ether, ethyl acetate, methyl acetate, 1,4-butyne-diol, and the like.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

The total daily dose of the compounds of this invention administered to a human or lower animal may range from about 0.000001 to about 10 mg/kg/day. For purposes of oral administration, more preferable doses can be in the range of from about 0.001 to about 1 mg/kg/day. For topical administration, more preferable doses can be in the range of 0.00001 mg/kg/day to about 5 mg/kg/day. If desired, the effective daily dose can be divided into multiple doses for purposes of administration, e.g., two to four separate doses per day.

Synthetic Methods

The following schemes and written descriptions provide general details regarding the preparation of the compounds of the invention. The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of formula I, IA, IB, IC or ID.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in conventional manner. See, for example, those described in 'Greene's Protective Groups in Organic Synthesis' by Theodora W Greene and Peter G M Wuts, third edition, (John Wiley and Sons, 1999), in particular chapters 7 ("Protection for the Amino Group") and 5 ("Protection for the Carboxyl Group"), incorporated herein by reference, which also describes methods for the removal of such groups.

All of the derivatives of formula I can be prepared by the procedures described in the general methods presented below or by routine modifications thereof. The present invention also encompasses any one or more of these processes for preparing the derivatives of formula I, IA, IB, IC or ID, in addition to any novel intermediates used therein. The person skilled in the art will appreciate that the following reactions may be heated thermally or under microwave irradiation. It will be further appreciated that it may be necessary or desirable to carry out the transformations in a different order from that described in the schemes, or to modify one or more of the transformations, to provide the desired compound of the invention.

One skilled in the art will also recognize that some compounds of the invention are chiral and thus may be prepared as racemic or scalemic mixtures of enantiomers. Several methods are available and are well known to those skilled in the art for the separation of enantiomers. A preferred method for the routine separation of enantiomers is supercritical fluid chromatography employing a chiral stationary phase.

Compounds of formula I, IA, IB, IC or ID may be prepared from compounds A-1, A-2 and C-3 (A=n-propyl, 1-hydroxypropyl or 2-hydroxypropyl, or a protected form thereof), as illustrated by Scheme A. Compounds of formulae A-1, A-2 and C-3 are commercially available or may be synthesized by those skilled in the art according to the literature or preparations described herein. For these purposes, PG is a protecting group and typically is tert-butoxycarbonyl. Compounds of formula A-3 may be prepared from compounds of formulae A-1 and A-2 according to process step (i), an aromatic substitution reaction in the presence of an organic base. Preferred conditions comprise triethylamine in methanol at from 0° C. to room temperature. Compounds of formula A-5 may be prepared from compounds of formula A-3 according to process steps (ii) and (iii), a nucleophilic substitution reaction with compounds of formula C-3 under either Buchwald-Hartwig cross coupling conditions or mediated by acid and elevated temperatures followed by a deprotection reaction mediated by either an inorganic or organic acid. Typical Buchwald-Hartwig conditions comprise a suitable palladium catalyst with a suitable chelating phosphine ligand with an inorganic base in a suitable organic solvent at elevated temperatures either thermally or under microwave irradiation. Preferred conditions comprise either a) palladium(II) acetate and 2-dicyclohexylphosphino-2',4',6'-triisopropylbiphenyl or Xantphos™ with sodium tert-butoxide, b) potassium phosphate or cesium carbonate in DMA at from 120-140° C. under microwave irradiation or c) BrettPhos™ Pd G3 with cesium carbonate as base and either DMA or dioxane as solvent at 40° C. Typical acidic conditions comprise a suitable inorganic acid in a suitable alcoholic solvent at elevated temperatures either thermally or under microwave irradiation. Preferred conditions comprise concentrated hydrochloric acid in iso-propanol at 140° C. under microwave irradiation. Alternatively, the deprotection occurs in situ during process step (ii). Compounds of formula A-6 (A=n-propyl, 1-hydroxypropyl or 2-hydroxypropyl, or a protected form thereof) may be prepared from compounds of formula A-5 according to process step (iv), an amide bond formation reaction with compounds of formula BC(O)X, wherein X may be chloro, hydroxy, a suitable leaving group or anhydride (e.g., (S)-2,2-Difluorocyclopropane-1-carboxylic acid). Wherein compounds of formula BC(O)X are acid chlorides, preferred conditions comprise triethylamine in dichloromethane at room temperature. Wherein compounds of formula BC(O)X are carboxylic acids, activation of the carboxylic acid using a suitable organic base and a suitable coupling agent is employed. Preferred conditions comprise DIPEA or triethylamine with HATU in dichloromethane or DMF at room temperature.

prepared from compounds of formulae B-1 and BC(O)X according to process step (ii), an amide bond formation reaction as described in Scheme A. Compounds of formula A-6 may be prepared from compounds of formula B-2 according to process step (iii), a nucleophilic substitution reaction with compounds of formula C-3 under either Buchwald-Hartwig cross coupling conditions or mediated by acid and high temperatures as described in Scheme A.

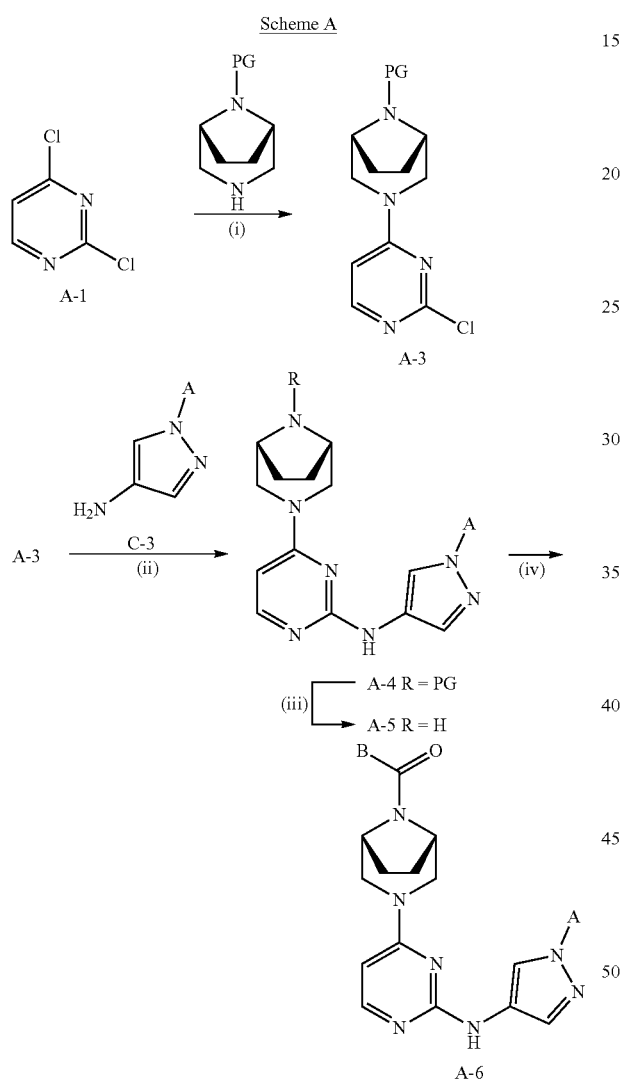

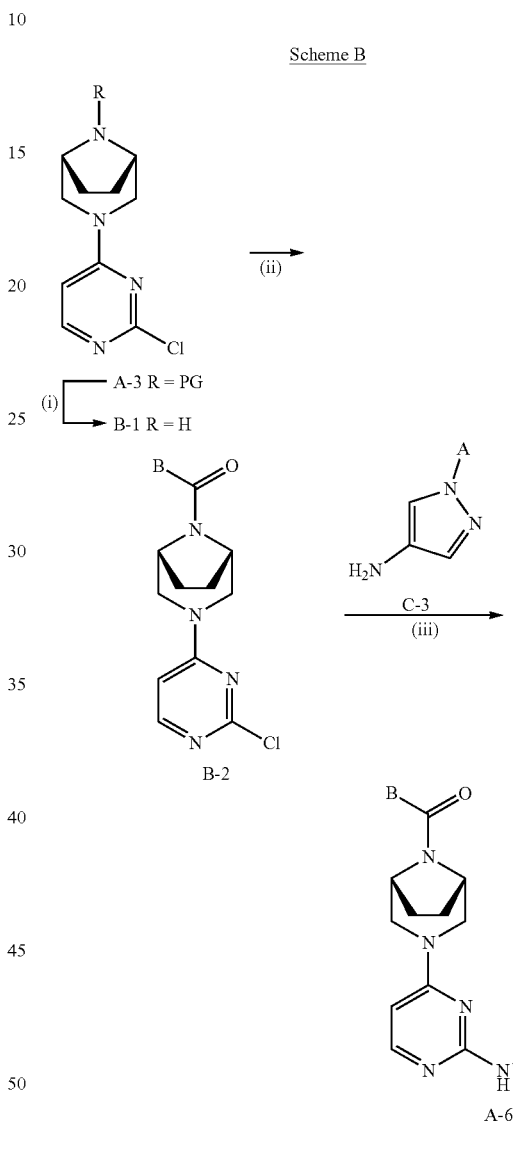

Alternatively, compounds of formula I, IA, IB, IC or ID may be prepared from compounds A-3 and C-3, as illustrated by Scheme B. Compounds of formula A-3 are prepared as described in Scheme A. Compounds of formula C-3 are commercially available or may be synthesized by those skilled in the art according to the literature or preparations described herein. Compounds of formula B-1 may be prepared from compounds of formula A-3 according to process step (i) a deprotection reaction mediated by either an inorganic or organic acid in a suitable organic solvent. Preferred conditions comprise hydrochloric acid or TFA in dioxane or DCM. Compounds of formula B-2 may be Compounds of formula C-3 employed in Scheme A and Scheme B may be prepared from compounds of formula C-1, as illustrated in Scheme C. The compound of formula C-1 is commercially available or may be synthesized by those skilled in the art according to the literature or preparations described herein. Compounds of formula C-2 may be prepared from compounds of formula C-1 according to process step (i) an alkylation reaction with an appropriately substituted alkyl halide of the formula AX where X is Cl, Br or I in the presence of an inorganic or organic base and a solvent such as DMF, or an addition reaction to an epoxide in the presence of an inorganic or organic base. Compounds of formula C-3 may be prepared from compounds of formula C-2 according to process step (ii) a reduction typically performed in the presence of a metal catalyst such as palladium or nickel, hydrogen gas at a pressure of 1-50 atmospheres, and a protic solvent such as methanol.

Scheme C

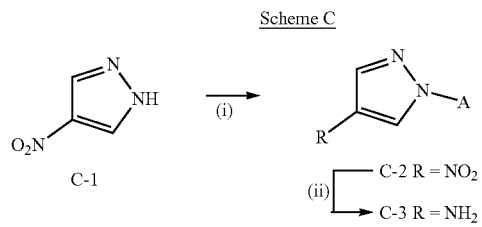

PREPARATIONS AND EXAMPLES

The following non-limiting Preparations and Examples illustrate the preparation of compounds and salts of the present invention. In the Examples and Preparations that are set out below, and in the aforementioned Schemes, the following abbreviations, definitions and analytical procedures may be referred to. Other abbreviations common in the art may also be used.

Compounds of the present invention were named using Chemdraw Professional™ version 18.0 (Perkin Elmer) or were given names which are consistent with IUPAC nomenclature. $^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g., s, singlet; d, doublet; t, triplet; q, quartet; m, multiplet; br, broad. The following abbreviations have been used for common NMR solvents: $CD_3CN$, deuteroacetonitrile; $CDCl_3$, deuterochloroform; DMSO-$d_6$, deuterodimethylsulfoxide; and $CD_3OD$, deuteromethanol. Where appropriate, tautomers may be recorded within the NMR data; and some exchangeable protons may not be visible. Some resonances in the NMR spectrum appear as complex multiplets because the isolate is a mixture of two conformers.

Mass spectra were recorded using electron impact ionization (EI), electrospray ionization (ESI) or atmospheric pressure chemical ionization (APCI). The observed ions are reported as MS m/z and may be positive ions of the compound [M]$^+$, compound plus a proton [MH]$^+$, or compound plus a sodium ion [MNa]$^+$. In some cases the only observed ions may be fragment ions reported as [MH-(fragment lost)]$^+$. Where relevant, the reported ions are assigned for isotopes of chlorine ($^{35}$Cl and/or $^{37}$Cl), bromine ($^{79}$Br and/or $^{81}$Br) and tin ($^{120}$Sn).

Wherein TLC, chromatography or HPLC has been used to purify compounds, one skilled in the art may choose any appropriate solvent or combination of solvents to purify the desired compound. Chromatographic separations (excluding HPLC) were carried out using silica gel adsorbent unless otherwise noted.

All reactions were carried out using continuous stirring under an atmosphere of nitrogen or argon gas unless otherwise noted. In some cases, reactions were purged with nitrogen or argon gas prior to the start of the reaction. In these cases, the nitrogen or argon gas was bubbled through the liquid phase of the mixture for the approximate specified time. Solvents used were commercial anhydrous grades. All starting materials were commercially available products. In some cases, starting materials were prepared according to reported literature procedures. It will be apparent to one skilled in the art that the word "concentrated" as used herein generally refers to the practice of evaporation of solvent under reduced pressure, typically accomplished by the use of a rotary evaporator.

The following abbreviations are used herein:
ACN: acetonitrile;
ATM: atmospheric pressure
BrettPhos™ Pd G3: [(2-Di-cyclohexylphosphino-3,6-dimethoxy-2',4',6'-triisopropyl-1,1'-biphenyl)-2-(2'-amino-1,1'-biphenyl)]palladium(II) methanesulfonate;
c: concentration
CDI: 1,1'-carbonyldiimidazole;
$Cs_2CO_3$: cesium carbonate;
DCM: dichloromethane
DIPEA: N, N-diisopropylethylamine;
DMA: N, N-dimethylacetamide;
DMF: N, N-dimethylformamide;
ESI: electrospray ionization;
EtOAc: ethyl acetate;
HATU: N-[(Dimethylamino)-1H-1,2,3-triazolo-[4,5-b]pyridine-1-ylmethylene]-N-methylmethanaminium hexafluorophosphate N-oxide;
HCl: hydrochloric acid;
HPLC: high pressure liquid chromatography;
HRMS: high resolution mass spectrum;
$H_2SO_4$: sulfuric acid;
kg: kilogram or kilograms
KOH: potassium hydroxide;
MeOH: methanol;
MIBK: methyl isobutyl ketone;
mg: milligram;
mL: milliliter;
mmol: millimole;
Mpa: megapascal;
MTBE: methyl tert-butyl ether;
NMT: not more than;
Pd/C: palladium on carbon;
TBAB: tetrabutylammonium bromide;
TFA: trifluoroacetic acid;
THF: tetrahydrofuran;
TLC: thin layer chromatography;
T3P: 2,4,6-tripropyl-1,3,5,2,4,6-trioxatriphosphorinane-2,4,6-trioxide;
Xantphos: 4,5-Bis(diphenylphosphino)-9,9-dimethylxanthene.

Preparation 1. (S)-2,2-difluorocyclopropane-1-carboxylic acid 2,2',2"-nitrilotris(ethan-1-ol) Salt

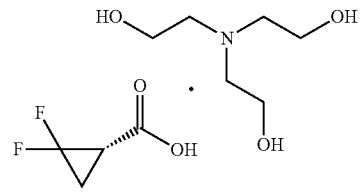

To a 100 mL reactor was added ACN (50.0 mL) and triethanolamine (12.2 g, 1.0 equivs). This solution was heated to 45° C., and a pre-mixed solution of (S)-2,2-difluorocyclopropane-1-carboxylic acid prepared as describe in preparation 68 of U.S. Pat. No. 9,663,526 (10.1 g, 1.0 equiv) in MTBE (50.0 mL, ~20% w/w) was added dropwise over 100 minutes. After addition, the reaction was held at 45° C. for 30 minutes, then cooled to 20° C. at a rate of 0.25° C./min. The mixture was granulated for 30 minutes, then filtered and washed with MTBE (40.0 mL), and dried under vacuum at 50° C. $^1$H NMR (400 MHz, DMSO-d$_6$) δ 6.85 (s, 4H), 3.61 (t, J=5.7 Hz, 6H), 2.97 (t, J=5.7 Hz, 6H), 2.38 (ddd, J=15.4, 10.8, 7.9 Hz, 1H), 1.84-1.62 (m, 2H). $^{13}$C NMR (101 MHz, DMSO-d$_6$) δ 169.0, 115.9, 113.1 (dd, J=285.9, 281.2 Hz), 113.1, 110.3, 57.4, 56.5, 27.7, 27.6 (dd, J=12.0, 9.2 Hz), 27.6, 27.5, 16.2, 16.1 (t, J=9.8 Hz), 16.0. mp: 82.4° C.

Preparation 2. 2,2-Difluorocyclopropane-1-(S)-carboxylate (R)—N-Benzyl-1-phenylethan-1-aminium Salt

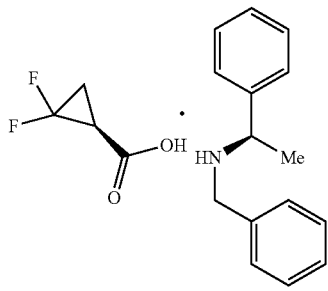

To a 250 mL vessel was added MTBE (134 mL), (S)-2, 2-difluorocyclopropane-1-carboxylic acid 2,2',2''-nitrilotris (ethan-1-ol) salt (20.0 g, 1.0 equiv), and a premixed solution of sulfuric acid (4.3 mL, 1.1 equivs) in water (86.0 mL). The mixture was stirred until all solids dissolved, and then the layers allowed to settle. The layers were separated, and the bottom (aqueous) layer was back-extracted with MTBE (58 mL). The combined organic layers were dried via azeotropic distillation to achieve a final concentration of (S)-2,2-difluorocyclopropane-1-carboxylic acid of ~15% (w/w) in MTBE. To this solution was added chiral amine (R)-(+)-N-benzyl-α-methylbenzylamine (13.0 g, 0.85 equivs) dropwise over ~1 hour. After ~25% of the amine had been added, the reaction was seeded with previously purified (R)—N-benzyl-1-phenylethan-1-amine (S)-2,2-difluorocyclopropane-1-carboxylate (50 mg, 0.002 equivs). After addition of the amine, the slurry was allowed to granulate, then filtered, and washed with MTBE (12.0 mL) that had been pre-chilled to 10° C., and the solids dried under vacuum at 50° C. The crude solids (10.57 g) were returned to the same vessel and ACN (35.0 mL) added. The slurry was heated to 80° C. to fully dissolve the solids. The solution was cooled to 22° C. at a rate of 0.2° C./min and allowed to granulate. The product was collected by filtration and washed with ACN (13.0 mL) before drying under vacuum at 50° C. $^1$H NMR (400 MHz, DMSO-d$_6$) δ 9.25 (s, 2H), 7.46 (d, J=6.9 Hz, 2H), 7.43-7.24 (m, 9H), 4.00 (q, J=6.7 Hz, 1H), 3.74 (d, J=13.3 Hz, 1H), 3.65 (s, 1H), 2.50-2.39 (m, 1H), 1.90-1.66 (m, 2H), 1.43 (d, J=6.7 Hz, 3H). $^{13}$C NMR (101 MHz, DMSO-d$_6$) δ 168.5, 142.4, 137.1, 129.3, 129.0, 128.7, 128.0, 127.9, 127.6, 116.0, 113.2, 113.1 (dd, J=286.1, 281.3 Hz), 110.3, 57.2, 49.8, 27.6, 27.5 (dd, J=12.0, 9.3 Hz), 27.4, 22.5, 16.2, 16.1 (t, J=9.8 Hz), 16.07. mp: 138.6° C.

Example 1

((S)-2,2-Difluorocyclopropyl)((1R,5S)-3-(2-((1-propyl-1H-pyrazol-4-yl)amino)pyrimidin-4-yl)-3,8-diazabicyclo[3.2.1]octan-8-yl)methanone (IA)

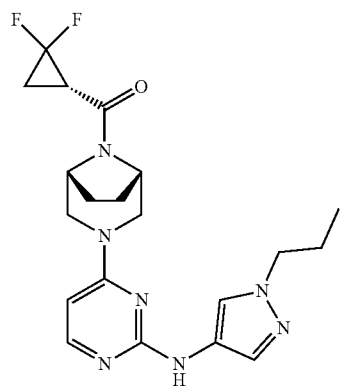 [SMILES: CCCn1cc(Nc2nccc(N3C[C@H]4CC[C@@H](C3)N4C(=O)[C@@H]3CC3(F)F)n2)cn1]

Step 1A. 4-Nitro-1-propyl-1H-pyrazole. This step was prosecuted in two parallel batches. Potassium carbonate (1.38 g, 9.99 mmol) was added in one portion to a 25° C. stirred mixture of 4-nitro-1H-pyrazole (360 g, 3.18 mol) in ACN (3 L), and the mixture was heated to around 50-60° C. 1-Iodopropane (595.3 g, 3.5 mol) was added to the mixture over a period of about 20 min. The resulting reaction mixture was stirred at 50-60° C. for about 2 hours. The reaction mixture was cooled to about 25° C. The two batches of reaction mixtures were combined, diluted with water (3 L) and concentrated under reduced pressure to remove most of the ACN. The resulting aqueous layer was extracted with EtOAc (4 L, 3×2 L). The combined organic extract was dried over sodium sulfate and filtered. The filtrate was concentrated under reduced pressure to afford 980.0 g (99%) of the title compound as an oil. $^1$H NMR (400 MHz, CDCl$_3$) δ 8.15 (s, 1H), 7.99 (s, 1H), 4.08 (t, J=7.2 Hz, 2H), 1.92-1.83 (m, 2H), 0.88 (t, J=7.2 Hz, 2H).

Step 1B. 1-Propyl-1H-pyrazol-4-amine hydrochloride. Pd/C (10% Pd, 71.06 g, 66.77 mmol) was added to a mixture of 4-nitro-1-propyl-1H-pyrazole (1.04 kg, 9.93 mol) in MeOH (5 L). The mixture was degassed and refilled with argon gas (3×). The mixture was warmed to 35° C. and stirred under a hydrogen gas atmosphere at around 2 Mpa for about 48 hours. Hydrogen gas was refilled as necessary as to keep the pressure at around 2 Mpa. The reaction mixture was filtered. The filtrate was concentrated to a solution (2.5 kg). The solution was added in portions to a solution of HCl in MeOH (5.99 mol, 2.35 L) at around 5-10° C. and stirred for about 1 hour. The mixture was concentrated under reduced pressure to afford a slurry (~1 L). EtOAc (500 mL) was added, and the mixture was stirred for about 5 min. The mixture was filtered, and the filter cake was washed with EtOAc (4×500 mL). The filter cake was dried under reduced pressure to afford 550 g of the title compound as a solid. MS m/z 126.1 [M+H]$^+$. $^1$H NMR (400 MHz, DMSO-d$_6$) δ 10.35 (br s, 3H), 7.94 (s, 1H), 7.51 (s, 1H), 4.05 (t, J=8.0 Hz, 2H), 1.78-1.69 (m, 2H), 0.79 (t, J=8.0 Hz, 3H).

Step 1C. tert-Butyl (1R,5S)-3-(2-Chloropyrimidin-4-yl)-3,8-diazabicyclo[3.2.1]-octane-8-carboxylate. The title compound was purchased from STA Pharmaceutical Hong Kong Limited.

Step 1D. 4-((1R,5S)-3,8-Diazabicyclo[3.2.1]octan-3-yl)-N-(1-propyl-1H-pyrazol-4-yl)pyrimidin-2-amine. To an 1 L OptiMax™ reaction vessel charged with 50 mL isopropanol and 375 mL water was added tert-butyl (1R,5S)-3-(2-chloropyrimidin-4-yl)-3,8-diazabicyclo[3.2.1]octane-8-carboxylate (50.00 g, 153.9 mmol) and 1-propyl-1H-pyrazol-4-amine hydrochloride (49.76 g, 1.20 equiv., 184.7 mmol) as solids. The suspension was stirred at 65° C. for about 2 hours before cooling to 45° C. A 50% KOH aqueous solution (77 mL, 6.0 equiv.) was added to the mixture and stirred at 35° C. for about 20 hours. The suspension was then cooled to 15° C., and solids collected by filtration to afford 43.51 g (90%) the title compound, as an off-white solid. MS m/z 314 [M+H]$^+$. $^1$H NMR (400 MHz, DMSO-d$_6$) δ 8.76 (s, 1H), 7.86 (d, J=5.9 Hz, 1H), 7.74 (s, 1H), 7.44 (s, 1H), 6.00 (d, J=6.1 Hz, 1H), 3.98 (t, J=6.9 Hz, 2H), 3.84 (s, 2H), 3.48 (d, J=4.7 Hz, 2H), 2.93 (d, J=11.8 Hz, 2H), 2.39 (s, 1H), 1.83-1.44 (m, 6H), 0.82 (t, J=7.4 Hz, 3H).

Step 1E. (S)-2,2-Difluorocyclopropane-1-carboxylic acid. A 2.0 L OptiMax™ reaction vessel was charged with 2,2-difluorocyclopropane-1-(S)-carboxylate (R)—N-benzyl-1-phenylethan-1-aminium salt (prepared as described in Preparation 2) (150 g, 450 mmol), MTBE (1 L), and concentrated sulfuric acid (27.2 mL, 0.495 mol) in water (945 mL). The mixture was stirred at 25° C. for about 1 hour. The aqueous layer was separated and extracted with MTBE (630 mL). The combined organic layers were concentrated to afford 56.7 g (95%) of the title compound as an oil.

Step 1F. ((S)-2,2-Difluorocyclopropyl)((1R,5S)-3-(2-((1-propyl-1H-pyrazol-4-yl)amino)pyrimidin-4-yl)-3,8-diazabicyclo[3.2.1]octan-8-yl)methanone. To a 1.0 L OptiMax reaction vessel charged with THF (595 mL) was added (S)-2,2-difluorocyclopropane-1-carboxylic acid (43.7 g, 1.25 equiv., 331 mmol). The solution was cooled to 0° C. before the addition of CDI (59.7 g, 1.35 equiv., 357 mmol) as a solid in small portions. After stirring at 0° C. for about 90 minutes, water (17.0 g, 17.0 mL, 944 mmol) was added via an addition funnel over 5 minutes. The mixture was stirred at 0° C. for about 20 minutes. 2-Hydroxypyridine N-oxide (1.47 g, 0.05 equiv., 13.2 mmol) and 4-((1R,5S)-3,8-diazabicyclo[3.2.1]octan-3-yl)-N-(1-propyl-1H-pyrazol-4-yl)pyrimidin-2-amine (85.0 g, 264 mmol) were added to the reaction mixture as solids. The reaction mixture was stirred at 0° C. for about 12 hours. The reaction mixture was diluted with 600 mL of MIBK and filtered through a thin layer of Celite™ to remove solid impurities. The filtrate was transferred to a separatory funnel, washed sequentially with 50% saturated sodium bicarbonate solution, 50% saturated ammonium chloride solution and 50% saturated brine. The organic phase was transferred to a 2 L OptiMax™ reactor and THF was removed by vacuum distillation at 70° C. Heptane (600 mL) was slowly added to the solution at 70° C., and it was stirred at 70° C. for about 2 hours to give a white suspension. Another 600 mL of heptane was charged to the suspension using a dosing pump over a 1 hour period. The resulting suspension was stirred at 70° C. for about 2 hours before cooling to 25° C. over about 3 hours. The mixture was stirred for another 8 hours at 25° C. The suspension was filtered to afford 97.6 g (88%) of the title compound as a white solid. HRMS (LC-ESI) calculated for C$_{20}$H$_{25}$F$_2$N$_7$O [(M+H)$^+$] m/z 418.2162, found 418.2159. $^1$H NMR (400 MHz, DMSO-d$_6$) δ 8.87 (s, 1H), 7.93 (d, J=5.9 Hz, 1H), 7.75 (s, 1H), 7.46 (d, J=8.5 Hz, 1H), 6.11 (dd, J=10.6, 6.0 Hz, 1H), 4.75-4.51 (m, 2H), 4.00 (t, J=6.9 Hz, 4H), 3.28-2.85 (m, 3H), 2.02-1.57 (m, 8H), 0.82 (t, J=7.4 Hz, 3H).

Powder X-Ray Diffraction Analysis Powder X-ray diffraction analysis was conducted using a Bruker AXS D8 Endeavor diffractometer equipped with a Cu radiation source. The divergence slit was set at 15 mm continuous illumination. Diffracted radiation was detected by a PSD-Lynx Eye detector, with the detector PSD opening set at 4.129 degrees. The X-ray tube voltage and amperage were set to 40 kV and 40 mA respectively. Data was collected in the Theta-Theta goniometer at the Cu wavelength from 3.0 to 40.0 degrees 2-Theta using a step size of 0.00997 degrees and a step time of 1.0 second. The antiscatter screen was set to a fixed distance of 1.5 mm. Samples were rotated at 15/min during collection. Samples were prepared by placing them in a silicon low background sample holder and rotated during collection. Data were collected using Bruker DIFFRAC™ Plus software and analysis was performed by EVA diffract plus software (v. 5.0.0.22). Generally, a threshold value of 1 and a width value of 0.235 were used to make preliminary peak assignments. The output of automated assignments was visually checked and peak positions were adjusted to the peak maximum. Peaks with relative intensity of 3% were generally chosen. The peaks which were not resolved or were consistent with noise were not selected. A typical error associated with the peak position of crystalline material, from PXRD, stated in USP, is up to +/−0.2° 2-Theta (USP-941).

TABLE 1

PXRD peak list for Compound IA.

| Angle (°) | Rel. Intensity (%) |
|---|---|
| 4.6 | 100 |
| 9.2 | 92 |
| 12.1 | 3 |
| 13.8 | 15 |
| 16.0 | 15 |
| 16.4 | 10 |
| 16.8 | 9 |
| 18.1 | 37 |
| 18.5 | 56 |
| 19.6 | 55 |
| 19.9 | 49 |
| 21.5 | 7 |
| 22.1 | 5 |
| 22.5 | 3 |
| 23.0 | 13 |
| 23.6 | 6 |
| 24.0 | 14 |
| 24.4 | 9 |
| 26.7 | 4 |
| 27.7 | 3 |
| 28.3 | 6 |
| 28.6 | 6 |
| 28.9 | 5 |
| 30.1 | 5 |
| 33.1 | 4 |
| 33.5 | 3 |

FIG. 1 is a powder X-ray diffraction analysis of crystalline ((S)-2,2-difluorocyclopropyl)((1R,5S)-3-(2-((1-propyl-1H-pyrazol-4-yl)amino)pyrimidin-4-yl)-3,8-diazabicyclo[3.2.1]octan-8-yl)methanone. Based on Table 1, crystalline Compound IA is characterized by an X-ray powder diffraction pattern with characteristic diffraction peaks at 4.6, 9.2, 18.5, and 19.6±0.2 degrees two theta.

Example 2. ((S)-2,2-Difluorocyclopropyl)((1R,5S)-3-(2-((1-((R)-2-hydroxypropyl)-1H-pyrazol-4-yl)amino)pyrimidin-4-yl)-3,8-diazabicyclo[3.2.1]octan-8-yl)methanone (IB)

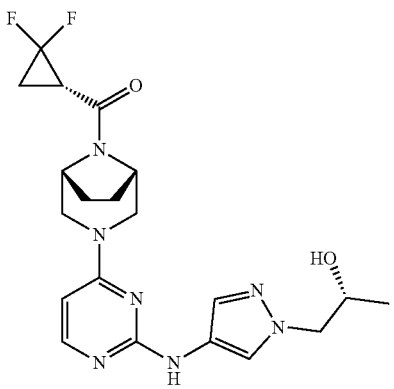 [SMILES: C[C@@H](O)Cn1cc(Nc2nccc(N3C[C@H]4CC[C@@H](C3)N4C(=O)[C@@H]3CC3(F)F)n2)cn1]

Step 2A. (R)-1-(4-Nitro-1H-pyrazol-1-yl)propan-2-ol. To a flask charged with (R)-(+)-propylene oxide (12 mL) was added 4-nitro-1H-pyrazole (4.0 g, 40 mmol) followed by $Cs_2CO_3$ (6.92 g, 21.2 mmol). The resulting mixture was stirred at 15° C. for about 32 hours. Water (30 mL) was added, and the mixture was extracted with EtOAc (3×40 ml). The combined organic layers were dried over sodium sulfate and filtered. The filtrate was concentrated under reduced pressure. The resulting residue was purified by silica gel chromatography eluting with an EtOAc:petroleum ether (1:1) solvent mixture to afford 5.3 g (90%) the title compound as a light-yellow oil. MS m/z 171.9 [M+H]$^+$. $^1$H NMR (400 MHz, CDCl$_3$) δ 8.23 (d, J=0.6 Hz, 1H), 8.09 (s, 1H), 4.34-4.26 (m, 1H), 4.25 (dd, J=13.8, 2.6 Hz, 1H), 4.06 (dd, J=13.7, 7.9 Hz, 1H), 2.47 (d, J=3.8 Hz, 1H), 1.28 (d, J=6.3 Hz, 3H).

Step 2B. (R)-1-(4-Amino-1H-pyrazol-1-yl)propan-2-ol. To a solution of (R)-1-(4-nitro-1H-pyrazole-1-yl)propan-2-ol (5.3 g, 31.0 mmol) in MeOH (60 mL) was added Pd/C (10% Pd, 659 mg, 0.02 equiv.). The resulting suspension was stirred under 1 atm pressure of hydrogen gas at room temperature for about 16 hours. The reaction mixture was filtered and the filtrate was concentrated under reduced pressure to afford 4.3 g (98%) of the title compound as a dark oil. MS m/z 142.1 [M+H]$^+$. $^1$H NMR (400 MHz, CDCl$_3$) δ 7.17 (d, J=0.9 Hz, 1H), 7.03 (d, J=0.9 Hz, 1H), 4.21-4.12 (m, 1H), 4.01 (dd, J=13.8, 2.8 Hz, 1H), 3.85 (dd, J=13.8, 8.0 Hz, 1H), 3.47 (s, 1H), 1.18 (d, J=6.4 Hz, 3H). $[α]^{20}_D$=−10.862 (c=0.2 g/100 mL, MeOH) Step 2C. tert-Butyl (1R,5S)-3-(2-Chloropyrimidin-4-yl)-3,8-diazabicyclo[3.2.1]octane-8-carboxylate. To an ice-cold solution of tert-butyl (1R,5S)-3,8-diazabicyclo[3.2.1]octane-8-carboxylate (6.0 g, 28.3 mmol) in MeOH (121 mL) was added triethylamine (7.9 ml, 56.5 mmol). After about 10 minutes, 2,4-dichloropyrimidine (4.6 g, 31.1 mmol) was added to the mixture in about two equal portions. The resulting mixture was stirred at around 15° C. for about 5 hours. The mixture was concentrated under reduced pressure to afford a slurry. The slurry was dissolved in dichloromethane (150 mL), washed with water (2×50 mL), dried over sodium sulfate, and filtered. The filtrate was concentrated under reduced pressure. The residue was purified by silica gel column chromatography eluted with a 0-50% EtOAc in petroleum ether to afford 8.3 g (90%) of the title compound as a white solid. MS m/z 325.1 [M+H]$^+$.

Step 2D. (1R,5S)-3-(2-Chloropyrimidin-4-yl)-3,8-diazabicyclo[3.2.1]octane. A solution of HCl in MeOH (60 mL, 4.0 M) was added to a solution of tert-butyl (1R,5S)-3-(2-chloropyrimidin-4-yl)-3,8-diazabicyclo[3.2.1]octane-8-carboxylate (10.3 g, 31.7 mmol) in MeOH (160 mL). After the addition, the mixture was stirred at around 15° C. for about 3 hours. The reaction was concentrated under reduced pressure. To the resulting solids was added water (40 mL) and cooled in an ice bath. An aqueous sodium hydroxide solution was slowly added to the stirred reaction mixture until a pH of around 10 was reached. The resulting slurry was extracted with dichloromethane (2×100 mL). The combined organic extract was dried over sodium sulfate and filtered. The filtrate was concentrated under reduce pressure to afford 6.6 g (87%) of the title compound as a white solid. MS m/z 225.0 [M+H]$^+$.

Step 2E. ((1R,5S)-3-(2-Chloropyrimidin-4-yl)-3,8-diazabicyclo[3.2.1]octan-8-yl)((S)-2,2-difluorocyclopropyl)methanone. T3P (8.86 g, 13.9 mmol, 50% solution in EtOAc) was slowly added to an ice-bath cooled solution of (1R,5S)-3-(2-chloropyrimidin-4-yl)-3,8-diazabicyclo[3.2.1]octane (1.56 g, 6.96 mmol), (S)-2,2-difluorocyclopropane-1-carboxylic acid 2,2',2"-nitrilotris(ethan-1-ol) salt (1.9 g, 6.96 mmol) prepared as described in Preparation 1 and triethylamine (4.9 mL, 34.8 mmol) in ACN (4 mL). The resulting reaction mixture was stirred in an ice bath for about 2 hours. An aqueous solution of NaHCO$_3$ (100 mL) was added to the ice-bath cooled mixture. The mixture was then diluted with water (500 mL) and EtOAc (500 mL). The organic layer was isolated, washed with brine (2×500 mL), dried over sodium sulfate and filtered. The filtrate was concentrated to afford 2.3 g (100%) of the title compound as a yellow solid. MS m/z 329.1 [M+H]$^+$. $[α]^{25}_D$=+38.010 (c=0.2 g/100 mL, MeOH).

Step 2F. ((S)-2,2-Difluorocyclopropyl)((1R,5S)-3-(2-((1-((R)-2-hydroxypropyl)-1H-pyrazol-4-yl)amino)pyrimidin-4-yl)-3,8-diazabicyclo[3.2.1]octan-8-yl)methanone. To a solution of ((1R,5S)-3-(2-chloropyrimidin-4-yl)-3,8-diazabicyclo[3.2.1]octan-8-yl)((S)-2,2-difluorocyclopropyl)methanone (500 mg, 1.52 mmol) in isopropanol (19.6 ml) was added (R)-1-(4-amino-1H-pyrazol-1-yl)propan-2-ol (258 mg, 1.83 mmol, 1.2 equiv) followed by concentrated hydrochloric acid (0.05 mL). The resulting solution was stirred at 76° C. for about 16 hours. The reaction mixture was concentrated under reduced pressure. The residue was taken up in water (20 mL), cooled in an ice-water bath, and neutralized to pH>7 by the addition of ammonium hydroxide. The solution was extracted with dichloromethane (2×30 mL). The combined organic extract was dried over sodium sulfate and filtered. The filtrate was concentrated under reduced pressure. The resulting crude product was purified by preparative HPLC (Welch Xtimate™ C18, 25 mm i.d.× 150 mm; water (0.05% ammonia hydroxide v/v)-ACN; 13-43%, 7 minutes) to afford 297.4 mg (45%) of the title compound (as a white solid after lyophilization. MS m/z 434.2 [M+H]$^+$. $^1$H NMR (400 MHz, DMSO-d$_6$) δ 8.90 (s, 1H), 7.93 (d, J=5.9 Hz, 1H), 7.79 (s, 1H), 7.44 (d, J=6.4 Hz, 1H), 6.14-6.10 (m, 1H), 4.88 (d, J=3.9 Hz, 1H), 4.73-4.51 (m, 2H), 4.14 (br s, 1H), 3.95-3.90 (m, 3H), 3.33-2.75 (m, 3H), 2.10-1.50 (m, 7H), 1.02 (d, J=4.6 Hz, 3H). $[α]^{20}_D$= +52.807 (c=0.2 g/100 mL, MeOH).

Example 3. ((S)-2,2-Difluorocyclopropyl)((1R,5S)-3-(2-((1-((S)-2-hydroxypropyl)-1H-pyrazol-4-yl)amino)pyrimidin-4-yl)-3,8-diazabicyclo[3.2.1]octan-8-yl)methanone (IC)

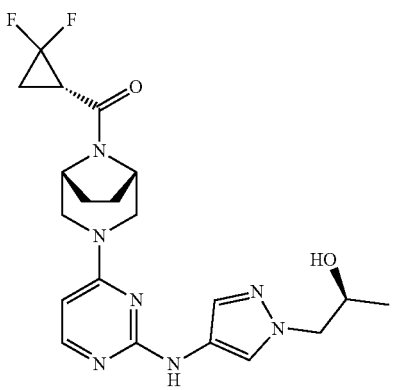 [SMILES: C[C@H](O)Cn1cc(Nc2nccc(N3C[C@H]4CC[C@@H](C3)N4C(=O)[C@@H]3CC3(F)F)n2)cn1]

Step 3A. (S)-1-(4-Nitro-1H-pyrazol-1-yl)propan-2-ol. To a flask charged with (S)-(−)-propylene oxide (6 mL) was added 4-nitro-1H-pyrazole (2.0 g, 20 mmol) followed by $Cs_2CO_3$ (5.76 g, 17.7 mmol). The resulting mixture was stirred at 15° C. for about 32 hours. Water (30 mL) was added, and the mixture was extracted with EtOAc (3×40 ml). The combined organic layers were dried over sodium sulfate and filtered. The filtrate was concentrated under reduced pressure. The resulting residue was purified on silica gel chromatography eluted with an EtOAc:petroleum ether (1:1) solvent mixture to afford 2.2 g (70%) of the title compound as a light-yellow oil. MS m/z 171.9 [M+H]$^+$. $^1$H NMR (400 MHz, CDCl$_3$) δ 8.23 (s, 1H), 8.09 (s, 1H), 4.31-4.24 (m, 1H), 4.22 (dd, J=13.8, 2.5 Hz, 1H), 4.06 (dd, J=13.7, 7.8 Hz, 1H), 2.49 (d, J=3.8 Hz, 1H), 1.28 (d, J=6.3 Hz, 3H).

Step 3B. (S)-1-(4-Amino-1H-pyrazol-1-yl)propan-2-ol. To a solution of (S)-1-(4-nitro-1H-pyrazole-1-yl)propan-2-ol (2.0 g, 11.7 mmol) in MeOH (60 mL) was added Pd/C (10% Pd, 249 mg, 0.2 equiv.). The resulting suspension was stirred under 1 atm of hydrogen gas at room temperature for about 16 hours. The reaction mixture was filtered and the filtrate concentrated under reduced pressure to give 1.5 g (91%) of the title compound as a dark oil. MS m/z 142.1 [M+H]$^+$. $^1$H NMR (400 MHz, CDCl$_3$) δ 7.19 (d, J=0.9 Hz, 1H), 7.03 (d, J=0.8 Hz, 1H), 4.18-4.10 (m, 1H), 4.02 (dd, J=13.8, 2.8 Hz, 1H), 3.86 (dd, J=13.8, 7.9 Hz, 1H), 3.47 (s, 1H), 1.21 (d, J=6.4 Hz, 3H). $[α]^{20}_D$=+38.201 (c=0.2 g/100 mL, MeOH).

Step 3C. ((S)-2,2-Difluorocyclopropyl)((1R,5S)-3-(2-((1-((S)-2-hydroxypropyl)-1H-pyrazol-4-yl)amino)pyrimidin-4-yl)-3,8-diazabicyclo[3.2.1]octan-8-yl)methanone. To a solution of ((1R,5S)-3-(2-chloropyrimidin-4-yl)-3,8-diazabicyclo[3.2.1]octan-8-yl)((S)-2,2-difluorocyclopropyl)methanone prepared as described in Step 2E (500 mg, 1.52 mmol) in isopropanol (21.7 mL) was added (S)-1-(4-amino-1H-pyrazol-1-yl)propan-2-ol (258 mg, 1.83 mmol, 1.2 equiv) followed by the addition of concentrated hydrochloric acid (1 mL). The resulting solution was stirred at 76° C. for about 16 hours. The reaction mixture was then concentrated under reduced pressure. The residue was taken up in water (20 mL), cooled with an ice-water bath, and neutralized and adjusted to pH>7 by the addition of ammonium hydroxide. The solution mixture was extracted with dichloromethane (2×30 ml). The combined organic extract was dried over sodium sulfate and filtered. The filtrate was concentrated under reduced pressure. The resulting residue was purified by preparative HPLC (Welch Xtimate™ C18, 25 mm i.d.×150 mm; water (0.05% ammonia hydroxide v/v)-ACN; 14-44%, 7 minutes) to afford 296.4 mg (45%) of the title compound (as a white solid after lyophilization. MS m/z 434.1 [M+H]$^+$. $^1$H NMR (400 MHz, DMSO-d$_6$) δ 8.90 (s, 1H), 7.93 (d, J=5.6 Hz, 1H), 7.80 (s, 1H), 7.44 (d, J=5.6 Hz, 1H), 6.13-6.09 (m, 1H), 4.88 (d, J=3.9 Hz, 1H), 4.69-4.58 (m, 2H), 4.14 (br s, 1H), 3.95-3.92 (m, 3H), 3.32-2.90 (m, 3H), 2.00-1.65 (m, 7H), 1.01 (d, J=6.0 Hz, 3H). $[α]^{20}_D$=+56.761 (c=0.2 g/100 mL, MeOH).

Example 4. ((S)-2,2-Difluorocyclopropyl)((1R,5S)-3-(2-((1-(3-hydroxypropyl)-1H-(pyrazol-4-yl)amino)pyrimidin-4-yl)-3,8-diazabicyclo[3.2.1]octan-8-yl)methanone (ID)

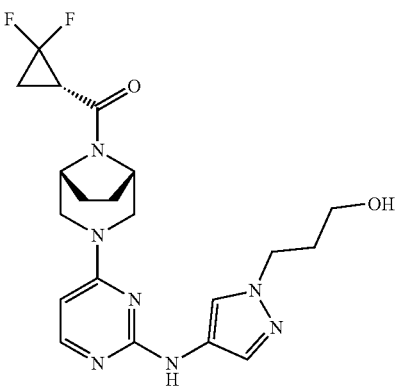 [SMILES: O=C([C@@H]1CC1(F)F)N1[C@@H]2CC[C@H]1CN(c1ccnc(Nc3cnn(CCCO)c3)n1)C2]

Step 4A. 3-(4-Nitro-1H-pyrazol-1-yl)propan-1-ol. To a mixture of 4-nitro-1H-pyrazole (1.13 g, 9.9 mmol) in dimethylformamide (20 mL) was added 3-bromopropanol (1.67 g, 12 mmol) and potassium carbonate (1.38 g, 9.99 mmol). The mixture was heated to 60° C. for about 16 h. The mixture was concentrated under reduced pressure. Water (100 mL) was added to the residue, and the mixture was extracted with EtOAc (3×100 mL). The combined organic extract was dried over sodium sulfate and filtered. The filtrate was concentrated under reduced pressure to afford 1.7 g (99%) of the title compound. MS m/z 171.9 [M+H]$^+$.

Step 4B. 3-(4-Amino-1H-pyrazol-1-yl)propan-1-ol. To a mixture of 3-(4-nitro-1H-pyrazol-1-yl)propan-1-ol (1.70 g, 9.93 mmol) in MeOH (19.0 mL) was added Pd/C (10% Pd, 0.60 g, 0.06 mmol). The mixture was stirred under 1 atm of hydrogen gas at room temperature for 16 h. The mixture was filtered and the filtrate was concentrated to afford 1.4 g (100%) of the title compound. $^1$H NMR (400 MHz, CDCl$_3$) δ 7.19-7.12 (m, 1H), 7.07-6.99 (m, 1H), 4.15 (t, J=6.5 Hz, 2H), 3.60 (t, J=5.9 Hz, 2H), 2.04-1.95 (m, 2H).

Step 4C. ((S)-2,2-Difluorocyclopropyl)((1R,5S)-3-(2-((1-(3-hydroxypropyl)-1H-pyrazol-4-yl)amino)pyrimidin-4-yl)-3,8-diazabicyclo[3.2.1]octan-8-yl)methanone. To a mixture of ((1R,5S)-3-(2-chloropyrimidin-4-yl)-3,8-diazabicyclo[3.2.1]octan-8-yl)((S)-2,2-difluorocyclopropyl)methanone prepared as described in Step 2E (600 mg, 1.8 mmol) in isopropanol (24 mL) was added 3-(4-amino-1H-pyrazol-1-yl)propan-1-ol (515 mg, 3.6 mmol) and concentrated hydrochloric acid (1 mL). The mixture was heated to 70° C. for about 16 hours. The mixture was concentrated under reduced pressure. The residue was dissolved in water (20 mL), and the pH was adjusted to >7 with ammonium hydroxide while being cooled in an ice water bath. The mixture was extracted with dichloromethane (2×30 mL). The organic extract was dried over sodium sulfate and filtered. The filtrate was concentrated. The residue was purified by preparative HPLC (Welch Xtimate™ C18, 25 mm i.d.×150 mm; water (0.05% ammonia hydroxide v/v)-ACN; 14-42%, 7 minutes) to afford 432 mg (55%) of the title compound as a white solid after lyophilization. MS m/z 434.3 [M+H]$^+$. $^1$H NMR (400 MHz, DMSO-d$_6$) δ 8.90 (s, 1H), 7.93 (d, J=5.6 Hz, 1H), 7.75 (s, 1H), 7.46 (d, J=4.8 Hz, 1H), 6.14-6.10 (m, 1H), 4.71-4.56 (m, 3H), 4.19 (br, 1H), 4.10 (t, J=6.9 Hz, 2H), 3.38 (q, J=5.9 Hz, 2H), 3.27-2.90 (m, 3H), 2.00-1.64 (m, 9H).

Assay Protocol

JAK Family Caliper Enzyme Assay

Compounds of the invention were evaluated by in vitro methods to determine their respective ability to inhibit the JAK kinases (TYK2, JAK1, JAK2, JAK3). Inhibitory activity was determined by using a microfluidic assay (LabChip 3000™ mobility shift technology, Caliper Life Science) to monitor phosphorylation of a synthetic peptide by the recombinant human kinase domain of each of the four members of the JAK family, JAK1, JAK2, JAK3 and TYK2. Reaction mixtures contained 1 μM of a fluorescently labeled synthetic peptide, a concentration less than the apparent $K_m$, and 1 mM ATP.

Compounds in DMSO solution were added to a 384-well plate. Reaction mixtures contained 10 mM HEPES, pH 7.4, 10 mM MgCl$_2$, 0.01% BSA, 0.0005% Tween 20™, 1 mM ATP and 1 μM peptide substrate. The JAK1 and TYK2 assays contained 1 μM of the IRStide peptide (5FAM-KKSRGDYMTMQID) and the JAK2 and JAK3 assays contained 1 μM of the JAKtide peptide (FITC-KG-GEEEEYFELVKK). The assays were initiated by the addition of 20 nM JAK1, 1 nM JAK2, 1 nM JAK or 1 nM TYK2 enzyme and were incubated at room temperature for three hours for JAK1, 60 minutes for JAK2, 75 minutes for JAK3 or 135 minutes for TYK2. Enzyme concentrations and incubation times were optimized for each new enzyme preps and were modified slightly over time to ensure 20% to 30% phosphorylation. The assays were stopped with 15 μL of 180 mM HEPES, pH 7.4, 20 mM EDTA, and 0.2% Coating Reagent 3. The assay plates were placed on a Caliper Life Science LC3000 instrument, and each well was sampled using appropriate separation conditions to measure the unphosphorylated and phosphorylated peptide.

Data Analysis

The data was collected using the HTS Well Analyzer software from Caliper Life Sciences. The data output for data analysis is the percent product converted calculated on peak height (Equation 1).

$$\% \text{ product converted} = 100*((\text{product})/(\text{product}+\text{substrate})) \quad \text{Equation 1:}$$

The percent effect at each compound concentration was calculated based on the positive and negative control well contained within each assay plate (Equation 2). The positive control wells contained a saturating concentration of a control compound that produced a level of phosphorylation comparable to background (i.e., completely inhibited JAK1, JAK2, JAK3 or TYK2). The negative control wells contained DMSO alone (at the same concentration as the compound wells) that was used to set the baseline activity in the assay (i.e., uninhibited JAK1, JAK2, JAK3 or TYK2).

$$\% \text{ effect} = 100*((\text{sample well}-\text{negative control})/(\text{positive control}-\text{negative control})) \quad \text{Equation 2:}$$

The percent effect was plotted against the compound concentration compound. An unconstrained sigmoid curve was fitted using a 4 parameter logistic model and the compound concentration required for 50% inhibition (IC50) was determined (Equation 3).

$$y=((\max-\min)/(1+((x/\text{IC}50)\hat{\ }s)))+\min \quad \text{Equation 3:}$$

Where max is the maximum asymptote (complete inhibition), min is the minimum asymptote (no inhibition) and s is the slope factor. IC$_{50}$ values are reported in nM for each compound in Table 1.

TABLE 1

| | IC$_{50}$ (nM) | | | |
|---|---|---|---|---|
| Compound | JAK1 | JAK2 | JAK3 | TYK2 |
| IA | 33 | 80 | >9,576 | 37 |
| IB | 59 | 223 | >10,000 | 82 |
| IC | 44 | 139 | >8.577 | 65 |
| ID | 47 | 81 | >9,285 | 30 |

HWB INF Alpha Induced STAT3 Phosphorylation Assay

Compounds of this invention were assessed for their ability to inhibit interferon alpha signalling in a human whole blood flow cytometry assay. Interferon alpha signals through TYK2 and JAK1. Test articles were prepared as 30 mM stocks in 100% DMSO, and then diluted to 10 mM. An 11-point 3 dilution series was created in DMSO with a top concentration of 5 mM. Further dilution was done by adding 4 μL of the above test article solutions into 96 μL of PBS with a top concentration of 400 μM. Human whole blood (HWB) was collected from healthy donors via vein puncture into Vacutainer™ collection tubes containing sodium heparin (Catalog No. 366480, Becton Dickinson, Franklin Lakes, N.J.). Blood was warmed to 37° C. prior to use. To a 96-well polypropylene plate (VWR 10755-246) 90 μL of HWB was added per well, followed by addition of 5 μL test article solutions prepared above to give a top concentration of 20 μM. The plate was mixed and incubated for 60 minutes at 37° C. To each well was added 5 μL of human IFN alpha (Universal Type I IFN, R&D Systems #11200-2; final concentration of 5000 U/ml) or D-PBS (unstimulated control), mixed and incubated 15 minutes at 37° C. The reaction was quenched by adding Lyse/Fix Buffer [BD Phosflow 5× Lyse/Fix Buffer (BD #558049)] to all wells at 700 μL/well and incubated for 20 minutes at 37° C.; after washing with FACS buffer [D-PBS (Invitrogen cat #14190) containing 0.1% BSA and 0.1% sodium azide], 400 μL ice cold 90% methanol/water was added to each well and incubated at 4° C. for 30 minutes. One more wash was done with FACS buffer and all samples were finally resuspended in 150 μL/well of Alexa Fluor 647 conjugated anti-phospho-STAT3 (pY705) antibody (BD #557815) at 1:150 dilution in FACS buffer. Samples were incubated overnight at 4° C.

Flow Cytometry

Samples were transferred to 96-well U bottom plates (Falcon #353077) and flow cytometric analysis was performed on an LSRFortessa equipped with a HTS plate loader (BD Biosciences). The lymphocyte population was gated for histogram analysis of pSTAT3. Background fluorescence was defined using unstimulated cells and a gate was placed at the foot of the peak to include ~0.5% gated population. The histogram statistical analysis was performed using FACSDiva version 8.0 (BD Biosciences) software. Relative fluorescence unit (RFU), which measures the level of phospho STAT, was calculated by multiplying the percent positive population and its mean fluorescence. Data from 11 compound concentrations (singlicate at each concentration) was normalized as a percentage of control based on the formula:

% of Control=100×(A−B)/(C−B)

where A is the RFU from wells containing compound and cytokine, B is the RFU from wells without cytokine and compound (minimum fluorescence) and C is the RFU from wells containing only cytokine (maximum fluorescence). Inhibition curves and IC50 values were determined using the Prism version 7 software (GraphPad, La Jolla, Calif.).

TABLE 2

| Compound | HWB IFN alpha IC$_{50}$ (nM) |
|---|---|
| IA | 66 |

Biomarker Modulation in Th2 Stimulated Ex Vivo Human Skin Assay

Compounds of this invention were assessed for their ability to modulate CXCL10 biomarker in Th2 stimulated ex vivo human skin following topical application.

Compounds were dissolved in a formulation comprised of:
10% w/w white petrolatum,
5% w/w mineral oil,
10% w/w emulsifying wax,
2% w/w oleyl alcohol,
46% w/w water,
15% w/w dietheylene glycol monoethyl ether,
10% w/w polytheylene glycol (PEG) 400, and
1% w/w 2-pehoxyethanol Freshly excised human skin from surgery specimens was cut with a dermatome to 750 μm thickness and mounted in a 7 mm static Franz cell for tissue culture such that the upper surface of the skin was exposed to air in the Franz cell donor chamber, and the bottom (dermis) was exposed to Cornification medium. A total of two skin donors were used (n=6 per treatment per donor). Incubations were carried out in a standard tissue culture incubator. Compound was dissolved in the indicated formulation at a concentration of 1% w/w and added apically to the skin at 10 μL per sample (approximately 18 μL per cm$^2$) at 4-6 replicates per donor. After 16 h media was replaced with stimulation cocktail containing anti-CD3 mAb, anti-CD28 mAb, IL-2, IL-4, IL-33 and TSLP. Incubation was continued for additional 24 hr at 37° C. Then skin was harvested, treated with RNALater solution and processed for RNA extraction and qPCR that was run in duplicates. MMP12, CCL26, CXCL10 and Filaggrin may be measured. Results for each sample were normalized to its own GAPDH internal standard which was not appreciably affected by stimulus or compound. Fold change was normalized to untreated sample. The results are summarized in Table 3 below and in FIG. 2.

TABLE 3

| Compound | % inhibition CXCL10 |
|---|---|
| IA | 94.2% |
| II | 72.4% |

$^a$Compound II is ((S)-2,2-difluorocyclopropyl)-((1R,5S)-3-(2-((1-methyl-1H-pyrazol-4-yl)amino)pyrimidin-4-yl)-3,8-diazabicyclo[3.2.1]octan-8-yl)methanone, disclosed in U.S. Pat. No. 9,663,526.

In Vitro Human Hepatocyte Clearance Assay

A high-throughput human hepatocyte substrate-depletion assay was performed in a 384-well formatted as described previously [Di et al., Eur. J. Med. Chem., 2012, 57, 441]. Briefly, the cryopreserved human hepatocytes were thawed and resuspended in Williams' E medium supplemented with HEPES and Na$_2$CO$_3$. The cells were counted using the trypan blue exclusion method. Test compounds were added to suspended human hepatocytes in Williams' E medium buffer and incubated at 37° C. in a humidified CO$_2$ incubator (75% relative humidity, 5% CO$_2$/air) for 4 hours. The final incubation contained 0.5 million cells/mL and 1 μM test compound in 15 μL total volume with 0.1% DMSO. At various time points (0, 3, 10, 30, 60, 120, and 240 minutes), an aliquot of the sample was taken and quenched with cold acetonitrile containing internal standard. The samples were centrifuged at 3000 rpm for 10 minutes at 4° C., and the supernatants were transferred to new plates, which were sealed before performing LC-MS/MS analysis. The apparent metabolic intrinsic clearance ($CL_{int,\, met,\, app}$) was determined based on the substrate-depletion half-life estimated from the ratio of the peak area response of each compound to that of the internal standard, as described earlier [Di et al., Eur. J. Med. Chem., 2012, 57, 441]. The results are summarized in Table 4 below.

TABLE 4

| Compound | HHEP CL$_{int,\, app}$ (μL/min/million cells) |
|---|---|
| IA | 8.6 |
| II | <0.6 |

$^a$Compound II is ((S)-2,2-difluorocyclopropyl)-((1R,5S)-3-(2-((1-methyl-1H-pyrazol-4-yl)amino)pyrimidin-4-yl)-3,8-diazabicyclo[3.2.1]octan-8-yl)methanone, disclosed in U.S. Pat. No. 9,663,526.

We claim:
1. A compound of formula I:

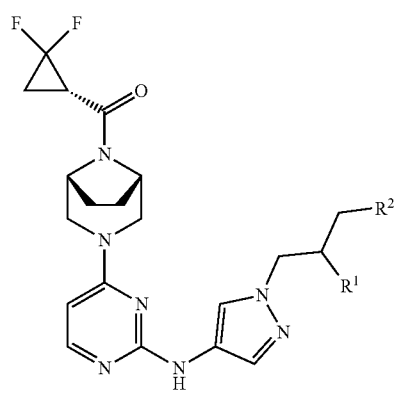

or a pharmaceutically acceptable salt thereof, wherein R$^1$ and R$^2$ are each independently hydrogen or hydroxy; wherein R$^1$ and R$^2$ are not both hydroxy.

2. The compound of claim 1 or a pharmaceutically acceptable salt thereof, wherein R$^1$ is hydroxy and R$^2$ is hydrogen.

3. The compound of claim 1 or a pharmaceutically acceptable salt thereof, wherein R$^1$ is hydrogen and R$^2$ is hydroxy.

4. A compound of formula IA:

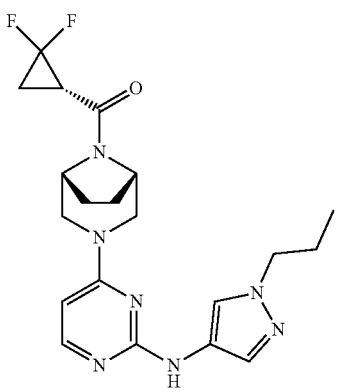

or a pharmaceutically acceptable salt thereof.

5. A compound of formula IB:

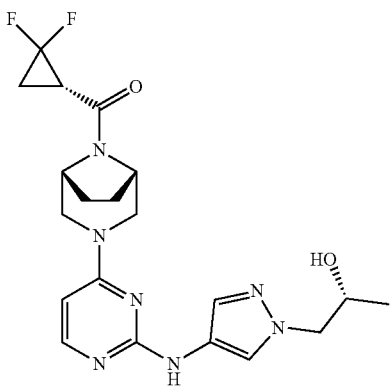

or a pharmaceutically acceptable salt thereof.

6. A compound of formula IC:

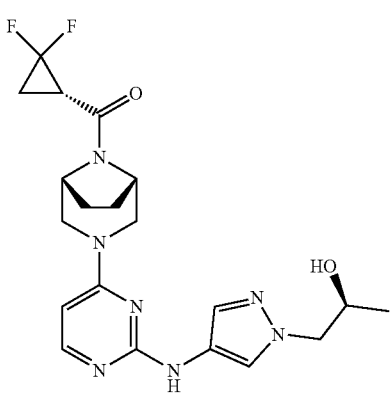

or a pharmaceutically acceptable salt thereof.

7. A compound of formula ID:

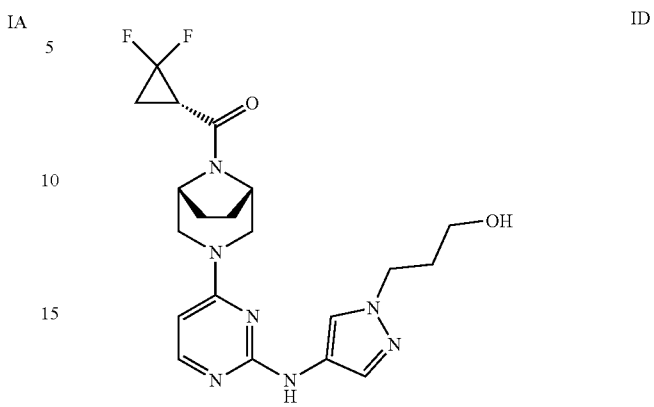

or a pharmaceutically acceptable salt thereof.

8. The compound of claim 1 selected from the group consisting of:
((S)-2,2-Difluorocyclopropyl)((1R,5S)-3-(2-((1-propyl-1H-pyrazol-4-yl)amino)pyrimidin-4-yl)-3,8-diazabicyclo[3.2.1]octan-8-yl)methanone;
((S)-2,2-Difluorocyclopropyl)((1R,5S)-3-(2-((1-((R)-2-hydroxypropyl)-1H-pyrazol-4-yl)amino)pyrimidin-4-yl)-3,8-diazabicyclo[3.2.1]octan-8-yl)methanone;
((S)-2,2-difluorocyclopropyl)((1R,5S)-3-(2-((1-((S)-2-hydroxypropyl)-1H-pyrazol-4-yl)amino)pyrimidin-4-yl)-3,8-diazabicyclo[3.2.1]octan-8-yl)methanone; and,
((S)-2,2-Difluorocyclopropyl)((1R,5S)-3-(2-((1-(3-hydroxypropyl)-1H-pyrazol-4-yl)amino)pyrimidin-4-yl)-3,8-diazabicyclo[3.2.1]octan-8-yl)methanone; or, a pharmaceutically acceptable salt thereof.

9. ((S)-2,2-Difluorocyclopropyl)((1R,5S)-3-(2-((1-propyl-1H-pyrazol-4-yl)amino)pyrimidin-4-yl)-3,8-diazabicyclo[3.2.1]octan-8-yl)methanone.

10. ((S)-2,2-Difluorocyclopropyl)((1R,5S)-3-(2-((1-((R)-2-hydroxypropyl)-1H-pyrazol-4-yl)amino)pyrimidin-4-yl)-3,8-diazabicyclo[3.2.1]octan-8-yl)methanone.

11. ((S)-2,2-Difluorocyclopropyl)((1R,5S)-3-(2-((1-(3-hydroxypropyl)-1H-pyrazol-4-yl)amino)pyrimidin-4-yl)-3,8-diazabicyclo[3.2.1]octan-8-yl)methanone.

12. ((S)-2,2-difluorocyclopropyl)((1R,5S)-3-(2-((1-((S)-2-hydroxypropyl)-1H-pyrazol-4-yl)amino)pyrimidin-4-yl)-3,8-diazabicyclo[3.2.1]octan-8-yl)methanone.

13. The compound or a pharmaceutically acceptable salt thereof according to claim 1, in an isolated form.

14. The compound or a pharmaceutically acceptable salt thereof of claim 1, in crystalline form.

15. A pharmaceutical composition comprising a compound of claim 1, or a pharmaceutically acceptable salt thereof, and a pharmaceutically acceptable carrier.

16. A method of treating a disease or condition for which a JAK1 inhibitor is indicated, wherein the disease or condition is selected from inflammation, autoimmune disease, neuroinflammation, arthritis, rheumatoid arthritis, spondyloarthropathies, systemic lupus erythematous, lupus nephritis, osteoarthritis, gouty arthritis, pain, fever, pulmonary sarcoidosis, silicosis, cardiovascular disease, atherosclerosis, myocardial infarction, thrombosis, congestive heart failure and cardiac reperfusion injury, cardiomyopathy, stroke, ischemia, reperfusion injury, brain edema, brain trauma, neurodegeneration, liver disease, inflammatory bowel disease, Crohn's disease, ulcerative colitis, nephritis, retinitis, retinopathy, macular degeneration, glaucoma, type 1 diabetes, type 2 diabetes, diabetic neuropathy, viral and bacterial infection, myalgia, endotoxic shock, toxic shock syndrome, osteoporosis, multiple sclerosis, endometriosis, menstrual cramps, vaginitis, candidiasis, cancer, fibrosis, obesity, muscular dystrophy, polymyositis, dermatomyositis, autoimmune hepatitis, primary biliary cirrhosis, primary sclerosing cholangitis, vitiligo, Alzheimer's disease, skin flushing, eczema, psoriasis, atopic dermatitis, sunburn, keloid, hypertrophic scar, rheumatic diseases, urticaria, discoid lupus, cutaneous lupus, central nervous system lupus, psoriatic arthritis, asthma, allergic asthma, type I interferonopathies, Aicardi-Goutières syndrome, primary progressive multiple sclerosis, relapsing remitting multiple sclerosis, non-alcoholic fatty liver disease, non-alcoholic steatohepatitis, scleroderma, alopecia areata, scarring alopecia, prurigo, prurigo nodularis, CPUO, lichen diseases, lichen planus, Steven's Johnson's syndrome, spondylopathy, myositis, vasculitis, pemphigus, lupus, major depression disorder, allergy, dry eye syndrome, transplant rejection, septic shock, cardiopulmonary dysfunction, acute respiratory disease, ankylosing spondylitis, cachexia, chronic graft-versus-host disease, acute graft-versus-host disease, Celiac Sprue, idiopathic thrombocytopenic thrombotic purpura, thrombotic thrombocytopenic purpura, myasthenia gravis, Sjogren's syndrome, epidermal hyperplasia, cartilage inflammation, bone degradation, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile Reter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, enteropathic arthritis, reactive arthritis, Reter's Syndrome, myolitis, polymyolitis, dermatomyolitis, polyarteritis nodosa, Wegener's granulomatosis, arteritis, polymyalgia rheumatica, sarcoidosis, sclerosis, primary biliary sclerosis, sclerosing cholangitis, dermatitis, Still's disease, chronic obstructive pulmonary disease, Guillain-Barre disease, Graves' disease, Addison's disease, Raynaud's phenomenon, psoriatic epidermal hyperplasia, plaque psoriasis, guttate psoriasis, inverse psoriasis, pustular psoriasis, erythrodermic psoriasis, an immune disorder associated with or arising from activity of pathogenic lymphocytes, noninfectious uveitis, Behcet's disease and Vogt-Koyanagi-Harada syndrome, comprising administering to a subject in need thereof a therapeutically effective amount of a compound of claim 1, or a pharmaceutically acceptable salt thereof.

17. The method of claim 16 wherein the compound is selected from the group consisting of:
   ((S)-2,2-Difluorocyclopropyl)((1R,5S)-3-(2-((1-propyl-1H-pyrazol-4-yl)amino)pyrimidin-4-yl)-3,8-diazabicyclo[3.2.1]octan-8-yl)methanone;
   ((S)-2,2-Difluorocyclopropyl)((1R,5S)-3-(2-((1-((R)-2-hydroxypropyl)-1H-pyrazol-4-yl)amino)pyrimidin-4-yl)-3,8-diazabicyclo[3.2.1]octan-8-yl)methanone;
   ((S)-2,2-difluorocyclopropyl)((1R,5S)-3-(2-((1-((S)-2-hydroxypropyl)-1H-pyrazol-4-yl)amino)pyrimidin-4-yl)-3,8-diazabicyclo[3.2.1]octan-8-yl)methanone; and,
   ((S)-2,2-Difluorocyclopropyl)((1R,5S)-3-(2-((1-(3-hydroxypropyl)-1H-pyrazol-4-yl)amino)pyrimidin-4-yl)-3,8-diazabicyclo[3.2.1]octan-8-yl)methanone; or, a pharmaceutically acceptable salt thereof.

18. The method of claim 16 wherein the compound is ((S)-2,2-difluorocyclopropyl)((1R,5S)-3-(2-((1-propyl-1H-pyrazol-4-yl)amino)pyrimidin-4-yl)-3,8-diazabicyclo[3.2.1]octan-8-yl)methanone; or, a pharmaceutically acceptable salt thereof, in an isolated form.

19. The method of claim 16 wherein the compound is ((S)-2,2-Difluorocyclopropyl)((1R,5S)-3-(2-((1-(3-hydroxypropyl)-1H-pyrazol-4-yl)amino)pyrimidin-4-yl)-3,8-diazabicyclo[3.2.1]octan-8-yl)methanone; or, a pharmaceutically acceptable salt, in an isolated form.

20. A pharmaceutical combination comprising a compound in isolated form, or a pharmaceutically acceptable salt thereof, of claim 1, or a pharmaceutically acceptable salt thereof, and one or more additional pharmacologically active compounds.

\* \* \* \* \*